(12) United States Patent
Abe et al.

(10) Patent No.: US 6,566,548 B1
(45) Date of Patent: May 20, 2003

(54) MOLECULAR COMPOUNDS CONTAINING NOVEL CARBOXYLIC ACID DERIVATIVES AS THE CONSTITUENT COMPOUND

(75) Inventors: Satoru Abe, Chiba (JP); Hiroshi Suzuki, Chiba (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/806,601

(22) PCT Filed: Oct. 7, 1999

(86) PCT No.: PCT/JP99/05538

§ 371 (c)(1),
(2), (4) Date: Mar. 29, 2001

(87) PCT Pub. No.: WO00/20372

PCT Pub. Date: Apr. 13, 2000

(30) Foreign Application Priority Data

Oct. 8, 1998 (JP) .......................................... 10-286543

(51) Int. Cl.$^7$ .................................................. C07C 69/76
(52) U.S. Cl. ......................... 560/76; 560/96; 560/101; 562/468; 562/473; 562/480; 562/491; 562/488
(58) Field of Search ........................... 560/76, 96, 101; 562/468, 473, 480, 488, 491

(56) References Cited

U.S. PATENT DOCUMENTS 3,384,658 A 5/1968 McCracken et al.
4,644,021 A 2/1987 Toda et al.

FOREIGN PATENT DOCUMENTS

| JP | 62022701 | 1/1987 |
| JP | 3279373 | 12/1991 |
| JP | 6166646 | 6/1994 |

OTHER PUBLICATIONS

E. Clar and C. C. Mackay, "Circobiphenyl And The Attempted Synthesis Of 1:14, 3:4, 7:8, 10:11–Tetrabenzoperopyrene," Tetrahedron, Pergamon Press (Great Britain), p. 6041–6047, (May 9, 1972).

*Primary Examiner*—Paul J. Killos
(74) *Attorney, Agent, or Firm*—Dennis G. LaPointe

(57) ABSTRACT

Novel molecular compounds containing carboxylic acid derivatives represented by general formula (I) or (II) as the constituent compound and exhibiting excellent performances in various technical fields including selective separation of useful substances, chemical stabilization, nonvolatilization, prolongation of release and powderization, wherein X is $(CH_2)n$ or p-phenylene; n is 0, 1, 2 or 3; $R_1$ to $R_8$ and $R_{13}$ to $R_{20}$ are each hydrogen, $C_1$–$C_6$ alkyl, $C_2$–$C_4$ alkenyl, phenyl optionally substituted with $C_1$–$C_6$ alkyl, halogeno or $C_1$–$C_6$ alkoxy; and $R_9$ to $R_{12}$ and $R_{21}$ to $R_{24}$ are each hydrogen, $C_1$–$C_6$ alkyl, $C_2$–$C_4$ alkenyl, $C_{11}$–$C_{12}$ aralkyl or an alkali metal.

19 Claims, 16 Drawing Sheets

MOLECULAR COMPOUNDS CONTAINING NOVEL CARBOXYLIC ACID DERIVATIVES AS THE CONSTITUENT COMPOUND

This a 371 of PCT/JP99/05538 Oct. 7, 1999.

FIELD OF INVENTION

The present invention relates to novel carboxylic acid derivatives, molecular compounds containing the said carboxylic acid derivatives as constituent compounds, and others. In more detail, the present invention relates to novel carboxylic acid derivatives having tetrakisphenyl skeleton and processes for the preparation thereof, molecular compounds containing the said carboxylic acid derivatives as constituent compounds and processes for the preparation thereof, and coordination compounds with the said carboxylic acid derivatives as ligands.

BACKGROUND ART

Molecular compounds are compounds that two or more compounds are bound through relatively weak interactions other than covalent bonds, represented by hydrogen bonds or van der Waals forces. The molecular compounds have a property to dissociate into the original individual constituent compounds by simple operations, and are expected to have applications to technological fields such as selective separation of useful substances, chemical stabilization, nonvolatilization, prolongation of release and powderization in recent years.

An actual example of the molecular compounds is a clathrate compound. For example, clathrate compounds of 5-chloro-2-methyl-4-isothiazolin-3-one or the like with 1,1,6,6-tetraphenyl-2,4-hexadiyn-1,6-diol or 1,1-di(2,4-dimethylphenyl)-2-propyn-1-ol have been described in Japanese Patent Laid-open No. Sho 61-53201, and with 1,1'-bis-2-naphthol in Japanese Patent Laid-open No. Sho 62-22701. Japanese Patent Laid-open No. Hei 3-279373 has reported clathrate compounds of bisphenol compounds and isothiazolone compounds. Furthermore, clathrate compounds of tetrakisphenols and various organic compounds have been disclosed in Japanese Patent Laid-open No. Hei 6-166646.

However, conventional technology has not yet found clathrate compounds with very satisfactory performances in selective separation of useful substances, chemical stabilization, nonvolatilization, prolongation of release, powderization and others, because of easy destruction due to changes in external factors such as heat or pH, easy dissociation in liquids and other problems.

It is an object of the present invention to provide novel molecular compounds containing carboxylic acid derivatives with tetrakisphenyl skeleton as constituent compounds and having excellent performance in such technological fields as selective separation of useful substances, chemical stabilization, nonvolatilization, prolongation of release and powderization, and novel coordination compounds useful as solid catalysts.

DISCLOSURE OF THE INVENTION

To solve the above-mentioned problems earnest studies were carried out. As a result it was found that a molecular compound containing, as a constituent compound, a carboxylic acid derivative with a specific tetrakisphenyl skeleton of which carboxyl groups forming rigid hydrogen bonds by two-point interactions are arranged divergently, exhibits extremely excellent performances in such technological fields as selective separation of useful substances, chemical stabilization, nonvolatilization, prolongation of release and powderization. Thus the present invention has been completed.

That is, the present invention relates to carboxylic acid derivatives represented by the following Formula (I) or (II) [wherein, in Formulae (I) and (II), X is $(CH_2)_n$ or p-phenylene; n is 0, 1, 2 or 3; $R_1$ to $R_8$ and $R_{13}$ to $R_{20}$ are each hydrogen, $C_1$ to $C_6$ alkyl, $C_2$ to $C_4$ alkenyl, phenyl optionally substituted with $C_1$ to $C_6$ alkyl, halogen or $C_1$ to $C_6$ alkoxy; $R_9$ to $R_{12}$ and $R_{21}$ to $R_{24}$ are each hydrogen, $C_1$ to $C_6$ alkyl, $C_2$ to $C_4$ alkenyl, $C_7$ to $C_{12}$ aralkyl or alkali metal].

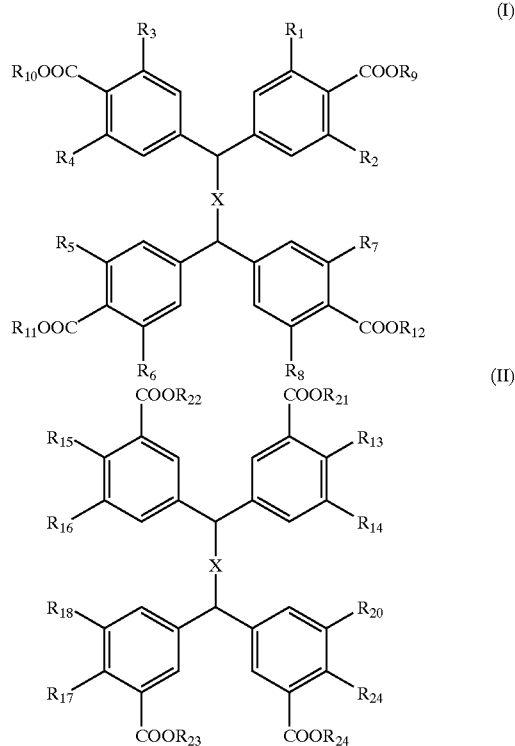

The present invention also relates to the said carboxylic acid derivatives represented by Formula (III) or (IV) below [wherein, in Formulae (III) and (IV), $R_{25}$ to $R_{32}$ and $R_{35}$ to $R_{42}$ are each hydrogen, $C_1$ to $C_6$ alkyl, $C_2$ to $C_4$ alkenyl, phenyl optionally substituted with $C_1$ to $C_6$ alkyl, halogen or $C_1$ to $C_6$ alkoxy; $R_{33}$, $R_{34}$, $R_{43}$ and $R_{44}$ are each hydrogen, $C_1$ to $C_6$ alkyl, $C_2$ to $C_4$ alkenyl, $C_7$ to $C_{12}$ aralkyl or alkali metal].

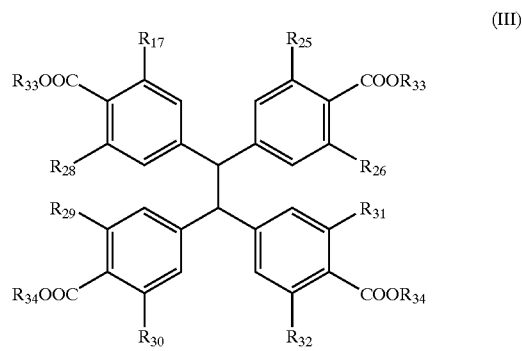

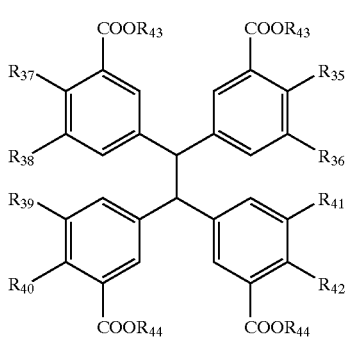

(IV)

The present invention also relates to processes for the preparation of the carboxylic acid derivatives represented by the above Formula (I) or (II), particularly by Formula (III) or (IV), characterized by the use of 1,1-bis(3-carboxyphenyl)ketone derivatives or 1,1-bis(4-carboxyphenyl)ketone derivatives.

The present invention also relates to molecular compounds such as clathrate compounds containing the carboxylic acid derivatives of the above Formula (I) or (II), particularly Formula (III) or (IV), as constituent compounds, and to molecular compounds such as the said clathrate compounds containing, as constituent compounds, the said carboxylic acid derivatives and antibacterial agents, antifungal agents, insecticides, noxious insect repellents, perfumes, deodorants, anti-fouling agents, curing agents and curing accelerators for coating materials, plastics and adhesives, natural essential oils, antioxidants, vulcanization accelerators or organic solvents that react with the said carboxylic acid derivatives to form clathrate compounds, and processes for the preparation of any of the above-mentioned molecular compounds.

Further, the present invention relates to coordination compounds having, as ligands, the carboxylic acid derivatives of the said Formula (I) or (II) wherein $R_9$ to $R_{12}$ and $R_{21}$ to $R_{24}$ are hydrogen or alkali metal.

The molecular compounds of the present invention refer to compounds that two or more constituent compounds able to exist alone and stably are bound by relatively weak interactions other than covalent bonds, represented by hydrogen bonds or van der Waals forces, and include hydrates, solvates, adducts, clathrate compounds and the like.

In the carboxylic acid derivatives of Formulae (I), (II), (III) and (IV) of the present invention, actual examples of substituents represented by $R_1$ to $R_8$, $R_{13}$ to $R_{20}$, $R_{25}$ to $R_{32}$ and $R_{35}$ to $R_{42}$ include hydrogen; straight-chain, branched-chain or cyclic $C_1$ to $C_6$ alkyl such as methyl, n-propyl, isopropyl, n-butyl, isobutyl, t-butyl, n-hexyl and cyclohexyl; $C_2$ to $C_4$ alkenyl such as vinyl, allyl, isopropenyl, 1-propenyl, 2-butenyl, 3-butenyl and 1,3-butadienyl; phenyl optionally substituted with $C_1$ to $C_6$ alkyl such as phenyl and p-methylphenyl; halogen such as fluorine, chlorine, bromine and iodine; and $C_1$ to $C_6$ alkoxy such as methoxy, ethoxy and t-butoxy.

In the carboxylic acid derivatives of Formulae (I), (II), (III) and (IV) of the present invention, actual examples of substituents represented by $R_9$ to $R_{12}$, $R_{21}$ to $R_{24}$, $R_{33}$, $R_{34}$, $R_{43}$ and $R_{44}$ include hydrogen; $C_1$ to $C_6$ alkyl such as methyl, ethyl, n-propyl and n-butyl; $C_2$ to $C_4$ alkenyl such as vinyl, allyl, isopropenyl, 1-propenyl, 2-butenyl, 3-butenyl and 1,3-butadienyl; aralkyl such as benzyl; and alkali metal such as sodium and potassium.

Of the carboxylic acid derivatives of Formula (I) or (II) of the present invention, tetrakiscarboxyphenylethane and its derivatives represented by Formula (III) or (IV) are particularly preferred from the viewpoints of performances such as selective separation of useful substances, chemical stabilization, nonvolatilization, prolongation of release and powderization.

Examples of tetrakisphenylcarboxylates of the invention include tetrakis(4-carboxyphenyl)ethane, tetrakis(4-carboxyphenyl)ethane tetramethyl ester, tetrakis(4-carboxyphenyl)ethane tetraethyl ester, tetrakis(4-carboxyphenyl)ethane tetra-n-propyl ester, tetrakis(4-carboxyphenyl)ethane tetrabenzyl ester, tetrakis(3,5-dimethyl-4-carboxyphenyl)ethane, tetrakis(3,5-dimethyl-4-carboxyphenyl)ethane tetramethyl ester, tetrakis(3,5-dimethyl-4-carboxyphenyl)ethane tetraethyl ester, tetrakis(3,5-dimethyl-4-carboxyphenyl)ethane tetra-n-propyl ester, tetrakis(3,5-dimethyl-4-carboxyphenyl)ethane tetrabenzyl ester, tetrakis(4-carboxyphenyl)ethane tetrasodium salt, tetrakis(4-carboxyphenyl)ethane tetrapotassium salt, tetrakis(3-carboxyphenyl)ethane, tetrakis(3-carboxyphenyl)ethane tetramethyl ester, tetrakis(3-carboxy-4,5-dimethylphenyl)ethane, tetrakis(3-carboxyphenyl)ethane tetraethyl ester, tetrakis(3-carboxyphenyl)ethane tetra-n-propyl ester, tetrakis(3-carboxyphenyl)ethane tetrabenzyl ester, tetrakis(3-carboxy-4,5-dimethylphenyl)ethane, tetrakis(3-carboxy-4,5-dimethylphenyl)ethane tetramethyl ester, tetrakis(3-carboxy-4,5-dimethylphenyl)ethane tetraethyl ester, tetrakis(3-carboxy-4,5-dimethylphenyl)ethane tetra-n-propyl ester, tetrakis(3,5-dimethyl-4-carboxyphenyl)ethane tetrabenzyl ester, tetrakis(3-carboxyphenyl)ethane tetrasodium salt and tetrakis(4-carboxyphenyl)ethane tetrapotassium salt.

Of the tetrakis(4-carboxyphenyl)ethane derivatives represented by Formula (III), those of center symmetry, where $R_{25}$ and $R_{32}$, $R_{26}$ and $R_{31}$, $R_{27}$ and $R_{30}$, and $R_{28}$ and $R_{29}$ are the same substituents, are prepared easily according to, for example, the following Reaction Stages (1) to (5). Of the tetrakis(3-carboxyphenyl)ethane derivatives represented by Formula (IV), those of center symmetry, where $R_{35}$ and $R_{37}$, $R_{36}$ and $R_{38}$, $R_{39}$ and $R_{41}$, and $R_{40}$ and $R_{42}$ are the same substituents, are prepared according to the same processes but using 1,1-bis(3-carboxyphenyl)ketone derivatives as starting materials.

Reaction Stage (1)

As shown in the following Reaction equation (1) (wherein $R_{25}$ to $R_{28}$ are hydrogen, $C_1$ to $C_6$ alkyl, $C_2$ to $C_4$ alkenyl or $C_7$ to $C_{12}$ aralkyl), a 1,1-bis(4-carboxyphenyl)ketone derivative is dissolved in an alcohol such as methyl alcohol or ethyl alcohol, an organic solvent such as N,N-dimethylformamide or dimethyl sulfoxide, or a dilute aqueous alkali solution such as sodium hydroxide. A reducing agent is introduced into the resulting solution to selectively convert the carbonyl group of the ketone to the alcohol at room temperature or while heating. When doing so, a reducing agent with relatively weak reducing power is preferably used. Particularly sodium borohydride or the like is preferred. A reaction temperature is arbitrarily chosen, and is preferably in the range between room temperature and 50° C.

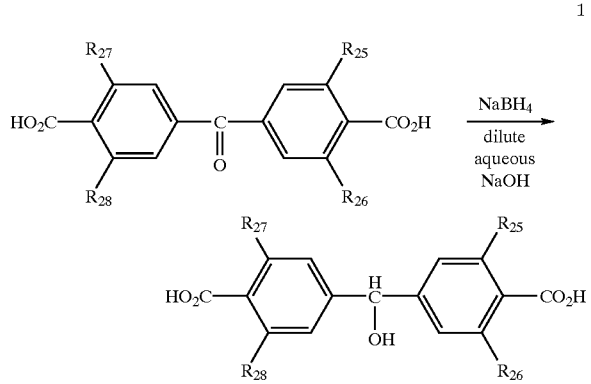

Reaction Stage (2)

As shown in the following Reaction equation (2), the hydroxyl group of the alcohol produced in Reaction Stage (1) is converted to a halogen, a leaving group, to give a halogenated compound. In halogenation, chlorination, bromination or iodination is usually carried out. Bromination is most favorable from the viewpoints of easy synthesis and the ease of the next reaction. For the bromination, 48% hydrobromic acid is preferably used. The alcohol is brominated while heating, using the hydrobromic acid 5 to 10 times in equivalent of the alcohol as hydrogen bromide. When doing so, the reaction temperature is preferably in the range between 90° C. and reflux. In case the alcohol does not dissolve in hydrobromic acid, it is preferable to use a hydrophilic solvent other than alcohols. Particularly acetic acid is preferably used.

Reaction Stage (3)

As shown in the following Reaction equation (3), the carboxyl groups of the bromide produced in Reaction Stage (2) are protected in the form of esters. When doing so, a simple $C_1$ to $C_6$ alkyl ester, such as methyl or ethyl, or a benzyl ester is preferred because of easy introduction and removal operations. These esterified compounds are obtained by reactions between carboxylic acids and the corresponding alcohols in the presence of mineral acid catalysts. It is more preferable to change to the chlorides of the carboxylic acids with thionyl chloride, followed by reactions with alcohols. In other words, a mixture of the bromide and an excessive amount of thionyl chloride is reacted, while heating, preferably at reflux, to give a carboxylic acid chloride.

As shown in the following Reaction equation (4), successively an esterification reaction is carried out using an alcohol, such as methyl alcohol or ethyl alcohol, in the presence of a base catalyst. When doing so, a preferred base catalyst is a weak basic amine, more preferably triethylamine, pyridine or the like. A reaction temperature is arbitrarily chosen, preferably in the range between room temperature and 40° C.

Reaction Stage (4)

As shown in the following Reaction equation (5), a metal reagent is acted on the halogenated alkyl diester compound synthesized in Reaction Stage (3) in a dehydrated organic solvent, while heating, to carry out a Wurtz-type condensation reaction to give an alkane. When doing so, a solvent, such as ethyl acetate, dimethyl sulfoxide or N,N-dimethylformamide, is preferably used. Zinc, magnesium, copper, iron, tin or the like is preferred as the metal reagent. The reaction is preferably carried out while heating, and more preferably at reflux.

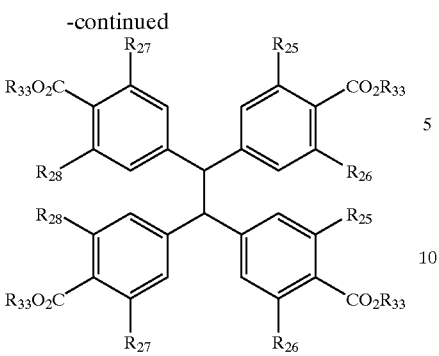
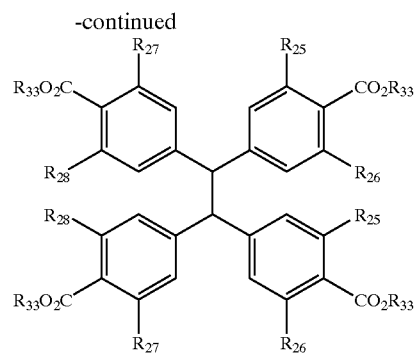

Reaction Stage (5)

As shown in the following Reaction equation (6), when the ester portions are converted to carboxylic acids, a reaction is carried out in a hydrophilic organic solvent, such as alcohol, acetone, 1,4-dioxane or N,N-dimethylformamide, using an aqueous solution of sodium hydroxide of about 1M concentration. When doing so, a reaction temperature can be arbitrarily chosen, and preferably in the range between 0° C. and 40° C.

On the other hand, of the tetrakis(4-carboxyphenyl)ethane derivatives represented by Formula (III), unsymmetrical compounds may be prepared according to the following Reaction equation (7): Two different diesters are synthesized in the same reaction stages as the above (1) to (3), and condensed by the method of Reaction Stage (4), followed by the operation of Reaction Stage (5). Of the tetrakis(3-carboxyphenyl)ethane derivatives represented by Formula (IV), unsymmetrical compounds can be prepared by the similar processes. A concrete process for the preparation of tetrakis(4-carboxyphenyl)ethane is described in Example 1 below.

7

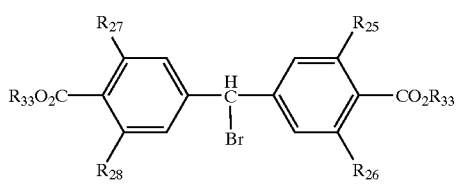
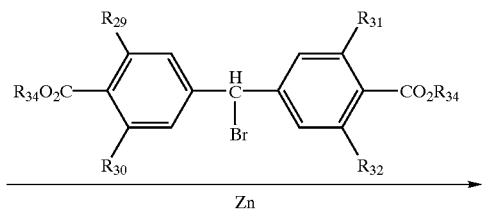
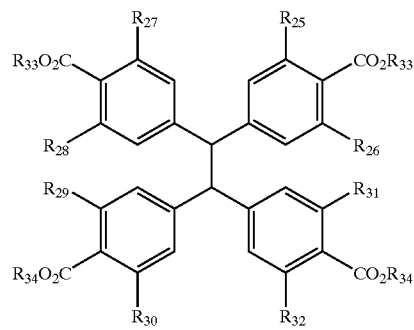

In the present invention, substances forming molecular compounds with the carboxylic acid derivatives of Formula (I) or (II), particularly formula (III) or (IV), can be any, if they can form molecular compounds with the carboxylic acid derivatives. Their actual examples include water; alcohols such as methanol, ethanol, isopropanol, n-butanol, n-octanol, 2-ethylhexanol, allyl alcohol, propagyl alcohol, 1,2-butanediol, 1,3-butanediol, 1,4-butanediol, cyclohexanediol, 2-bromo-2-nitropropan-1,3-diol, 2,2-dibromo-2-nitroethanol and 4-chlorophenyl-3-iodopropagylformal; aldehydes such as formaldehyde, acetaldehyde, n-butylaldehyde, propionaldehyde, benzaldehyde, phthalaldehyde, α-bromocinnamaldehyde and phenylacetaldehyde; ketones such as acetone, methyl ethyl ketone, diethyl ketone, dibutyl ketone, methyl isobutyl ketone, cyclohexanone, acetylacetone and 2-bromo-4'-hydroxyacetophenone; nitriles such as acetonitrile,

6

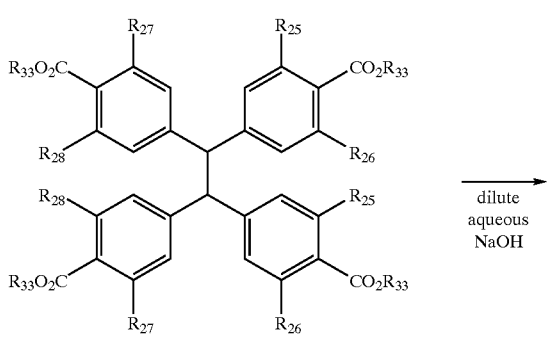

acrylonitrile, n-butylonitrile, malononitrile, phenylacetonitrile, benzonitrile, cyanopyridine, 2,2-dibromomethylglutaronitrile, 2,3,5,6-tetrachloroisophthalonitrile, 5-chloro-2,4,6-trifluoroisophthalonitrile and 1,2-dibromo-2,4-dicyanobutane; ethers such as diethyl ether, dibutyl ether, tetrahydrofuran, dioxane, tetrahydropyrane, dioxorane and trioxane; esters such as methyl acetate, ethyl acetate, butyl acetate, n-heptyl acetate and bis-1,4-bromoacetoxy-2-butene; sulfonamides such as benzene sulfonamide; amides such as N-methylformamide, N,N-dimethylformamide, dicyandiamide, dibromonitrilopropionamide, 2,2-dibromo-3-nitrilopropionamide and N,N-diethyl-m-toluamide; halogenated hydrocarbons such as dichloromethane, chloroform, dichloroethylene and tetrachloroethylene; lactams such as ε-caprolactam; lactones such as ε-caprolactone; oxiranes such as arylglycidyl ether; morpholines; phenols such as phenol, cresol, resorcinol and p-chloro-m-cresol; carboxylic acids and thiocarboxylic acids such as formic acid, acetic acid, propionic acid, oxalic acid, citric acid, adipic acid, tartaric acid, benzoic acid, phthalic acid and salicylic acid; sulfamic acids; thiocarbamic acids; thiosemicarbazides; ureas and thioureas such as urea, phenylurea, diphenylurea, thiourea, phenylthiourea, diphenylthiourea and N,N-dimethyldichlorophenylurea; isothioureas; sulfonylureas; thiols such as thiophenol, allylmercaptan, n-butylmercaptan and benzylmercaptan; sulfides such as benzyl sulfide and butylmethyl sulfide; disulfides such as dibutyl disulfide, dibenzyl disulfide and tetramethylthiuram disulfide; sulfoxides such as dimethyl sulfoxide, dibutyl sulfoxide and dibenzyl sulfoxide; sulfones such as dimethyl sulfone, phenyl sulfone, phenyl-(2-cyano-2-chlorovinyl)sulfone, hexabromodimethyl sulfone and diiodomethyl-para-tolyl sulfone; thiocyanic acids and isothiocyanic acids such as methyl thiocyanate and methyl isothiocyanate; amino acids such as glycine, alanine, leucine, lysine, methionine and glutamine; amide and urethane compounds; acid anhydrides; aromatic hydrocarbons such as benzene, toluene and xylene; alkanes, alkenes, alkynes, isocyanates such as butylisocyanate, cyclohexylisocyanate and phenylisocyanate; thiocyanates and isothiocyanates such as methylenebisthiocyanate and methylenebisisothiocyanate; nitro compounds such as tris(hydroxymethyl)nitromethane; acyclic aliphatic amines such as ammonia, methylamine, ethylamine, propylamine, butylamine, pentylamine, hexylamine, allylamine, hydroxylamine, ethanolamine, benzylamine, ethylenediamine, 1,2-propanediamine, 1,3-propanediamine, 1,4-butanediamine, 1,5-pentanediamine, 1,6-hexanediamine, diethylenetriamine, triethylenetetramine, tetraethylenepentamine, dipropylenediamine, N,N-dimethylethylenediamine, N,N'-dimethylethylenediamine, N,N-dimethyl-1,3-propanediamine, N-ethyl-1,3-propanediamine, trimethylhexamethylenediamine, alkyl-t-monoamine, menthanediamine, isophoronediamine, guanidine and N-(2-hydroxypropyl)aminomethanol, cyclic aliphatic amines such as cyclohexylamine, cyclohexanediamine, bis(4-aminocyclohexyl)methane, pyrrolidines, azetidines, piperizines, piperazines such as piperazine, N-aminoethylpiperazine and N,N'-dimethylpiperazine, and pyrrolines; aromatic amines such as aniline, N-methylaniline, N,N-dimethylaniline, o-phenylenediamine, m-phenylenediamine, p-phenylenediamine, diaminodiphenylmethane, diaminodiphenyl sulfone and m-xylylenediamine; modified polyamines such as epoxy compound-added polyamine, Michael-added polyamine, Mannich-added polyamine, thiourea-added polyamine and ketone-blocked polyamine; imidazoles such as imidazole, 2-methylimidazole, 2-ethylimidazole, 2-isopropylimidazole, 2-n-propylimidazole, 2-ethyl-4-methylimidazole, 1-benzyl-2-methylimidazole, 2-undecyl-1H-imidazole, 2-heptadecyl-1H-imidazole, 2-phenyl-1H-imidazole, 4-methyl-2-phenyl-1H-imidazole and 1-benzyl-2-methylimidazole; heterocyclic compounds containing nitrogen such as pyrrole, pyridine, picoline, pyrazine, pyridazine, pyrimidine, pyrazole, triazole, benzotriazole, triazine, tetrazole, purine, indole, quinoline, isoquinoline, carbazole, imidazoline, pyrroline, oxazole, piperine, pyrimidine, pyridazine, benzimidazole, indazole, quinazoline, quinoxaline, phthalimide, adenine, cytocine, guanine, uracil, 2-methoxycarbonylbenzimidazole, 2,3,5,6-tetrachloro-4-methanesulfonylpyridine, 2,2-dithio-bis-(pyridin-1-oxide), N-methylpyrrolidone, methyl 2-benzimidazole carbamate, 2-pyridinethiol-1-oxide sodium, hexahydro-1,3,5-tris(2-hydroxyethyl)-s-triazine, hexahydro-1,3,5-triethyl-s-triazine, 2-methylthio-4-t-butylamino-6-cyclopropylamino-s-triazine, N-(fluorodichloromethylthio)phthalimide, 1-bromo-3-chloro-5,5-dimethylhydantoin, 2-methoxycarbonylbenzimidazole and 2,4,6-trichlorophenylmaleimide; heterocyclic compounds containing oxygen such as furan, furfuryl alcohol, tetrahydrofurfuryl alcohol, furfurylamine, pyran, coumarin, benzofuran, xanthene and benzodioxane; heterocyclic compounds containing nitrogen and oxygen such as oxazole, isoxazole, benzoxazole, benzisoxazole, 5-methyloxazoline, 4-(2-nitrobutyl)morpholine and 4,4'-(2-ethyl-2-nitrotrimethylene)dimorpholine; heterocyclic compounds containing sulfur such as thiophene, 3,3,4,4-tetrahydrothiophen-1)1-dioxide, 4,5-dichloro-1,2-dithiolan-3-one, 5-chloro-4-phenyl-1,2-dithiolan-3-one and 3,3,4,4-tetrachlorotetrahydrothiophen-1,1-dioxide; heterocyclic compounds containing nitrogen and sulfur such as thiazole, benzothiazole, 5-chloro-2-methyl-4-isothiazolin-3-one, 2-methyl-4-isothiazolin-3-one, 4,5-dichloro-3-n-octylisothiazolin-3-one, 2-octyl-4-isothiazolin-3-one, 1,2-benzisothiazolin-3-one, 2-thiocyanomethylbenzothiazole, 2-(4-thiazolyl)benzimidazole and 2-thiocyanomethylbenzothiazole; steroids such as cholesterol; alkaloids such as brucine, quinine and theophylline; natural essential oils such as cineol, hinokitiol, menthol, terpineol, borneol, nopol, citral, citronellol, citronellal, geraniol, menthone, eugenol, linalool and dimethyloctanol; synthetic perfumes such as fragrant olive, jasmine and lemon; and vitamins and their related compounds such as ascorbic acid, nicotinic acid and nicotinamide.

The molecular compounds of the present invention can be prepared by mixing, directly or in solvents, the carboxylic acid derivatives of Formula (I) or (II), preferably Formula (III) or (IV), with substances forming molecular compounds with the said derivatives, such as those mentioned above. If the substances have low boiling points or high vapor pressures, the carboxylic acid derivatives of the present invention are reacted with the vapor of these substances to give target molecular compounds. It is possible to produce a molecular compound consisting of multiple constituents of three or more by a reaction of two or more substances with a carboxylic acid derivative of the present invention. Furthermore, a target molecular compound can be obtained by first preparing a molecular compound of a carboxylic acid derivative of the present invention with a substance, and then reacting the obtained molecular compound with another substance by such a method as mentioned above.

In the molecular compounds of the present invention, a ratio of constituent compounds may vary, depending on production conditions. The substances obtained by the above methods can be confirmed to be molecular compounds by thermal analyses (TG arid DTA), IR spectra, X-ray diffraction patterns, solid state NMR spectra and other means. The compositions of the molecular compounds can be confirmed by thermal analyses, $^1$H-NMR spectra, high performance liquid chromatography (HPLC), elementary analyses and other means.

The molecular compounds of the present invention are preferably crystalline, from the viewpoint of selective separation of useful substances, chemical stabilization, nonvolatilization, powderization and other functions and for the purposes of the stable production of molecular compounds of definite compositions and the like. Particularly crystalline clathrate compounds are more preferred. In this case, the same molecular compound may be polymorphic. The crystallinity can be confirmed by examining mainly X-ray diffraction patterns. The existence of polymorphism can be checked by thermal analyses, X-ray diffraction patterns, solid state NMR and other means. Here a clathrate compound refers to a substance that has holes of appropriate size in the inside of three-dimensional structures formed when atoms or molecules are bound and that contains other atoms or molecules which enter into the inside of the holes by means of non-covalent bond interactions at a certain definite composition ratio. The hole is not necessarily formed by one of the constituent compounds of the molecular compound alone, and may be formed only when a clathrate compound is prepared from two constituent compounds.

There are no particular restrictions on how to use the molecular compounds of the present invention. For example, two or more molecular compounds composing each different constituent compounds are mixed to use. The molecular compounds of the present invention may be used together with other substances, as long as target functions are not damaged. Another way to use the molecular compounds of the present invention is adding excipients or the like to the compounds for molding to granules or tablets. Further, the compounds may also be used to add to plastics, coating materials, and their raw materials or material compositions. The molecular compounds of the present invention may also be used, as they are, as starting materials for organic syntheses, or as specific reaction sites.

Clathrate compounds consisting of, for example, the carboxylic acid derivatives of Formulae (I), (II), (III) and (IV) as host compounds, with guest compounds including isothiazolone germicides such as 5-chloro-2-methyl-4-isothiazolin-3-one and 2-methyl-4-isothiazolin-3-one; antimicrobial agents, insecticides and moth proofing agents such as hinokitiol and 1,8-cineol; perfumes such as rosemary; anti-fouling agents such as isothiazolone compounds; catalysts including curing agents for epoxy resins such as phthalic anhydride, tetrahydrophthalic anhydride and 2-ethyl-4-methylimidazole and curing accelerators for epoxy resins such as 1,8-diazabicyclo(4,5,0)undecene-7; or organic solvents such as toluene, xylene and pyridine, are newly endowed with functions such as prolongation of release, reduction of skin irritation, chemical stabilization, nonvolatilization, powderization and selective separation of useful substances, in addition to the actions that the guest compounds have originally. Therefore, the clathrate compounds are very useful as germicides, antibacterial agents, insecticides, moth proofing agents, perfumes, anti-fouling agents, catalysts such as curing agents for epoxy resins and organic solvents, that have new characteristics.

The carboxyl groups of the carboxylic acid derivatives of the present invention function as bidentate ligands. The carboxylic acid derivatives of Formulae (I), (II), (III) and (IV) where $R_9$ to $R_{12}$, $R_{21}$, to $R_{24}$, $R_{33}$, $R_{34}$, $R_{43}$ and $R_{44}$ are hydrogen or alkali metal can form coordination compounds with metal ions. Examples of metal ions forming coordination compounds with the above carboxylic acid derivatives include copper, zinc, nickel and iron. There are no particular restrictions on processes for the preparation of coordination compounds containing, for example, the carboxylic acid derivatives where the above $R_9$ to $R_{12}$, $R_{21}$, to $R_{24}$, $R_{33}$, $R_{34}$, $R_{43}$ and $R_{44}$ are hydrogen as ligands. However, a novel coordination compound is usually prepared by reaction of a metal chloride, such as copper chloride or zinc chloride, with an alkali metal salt of a carboxylic acid derivative of the present invention to be a ligand, with stirring in water at room temperature for several ten minutes. Such novel coordination compounds can be used as various reaction catalysts, particularly as solid catalysts, because of the formation of net-shaped coordinated polymer compounds and steady capture of metal ions, such as copper, zinc, nickel or iron.

It can be confirmed by thermal analyses (TG and DTA), IR spectra, X-ray diffraction patterns and other means that the substances obtained by the methods are surely coordination compounds. The compositions of the coordination compounds can be confirmed by such means as thermal analyses, atomic absorption analyses and elementary analyses.

BEST FORM TO IMPLEMENT THE INVENTION

Figure 1:
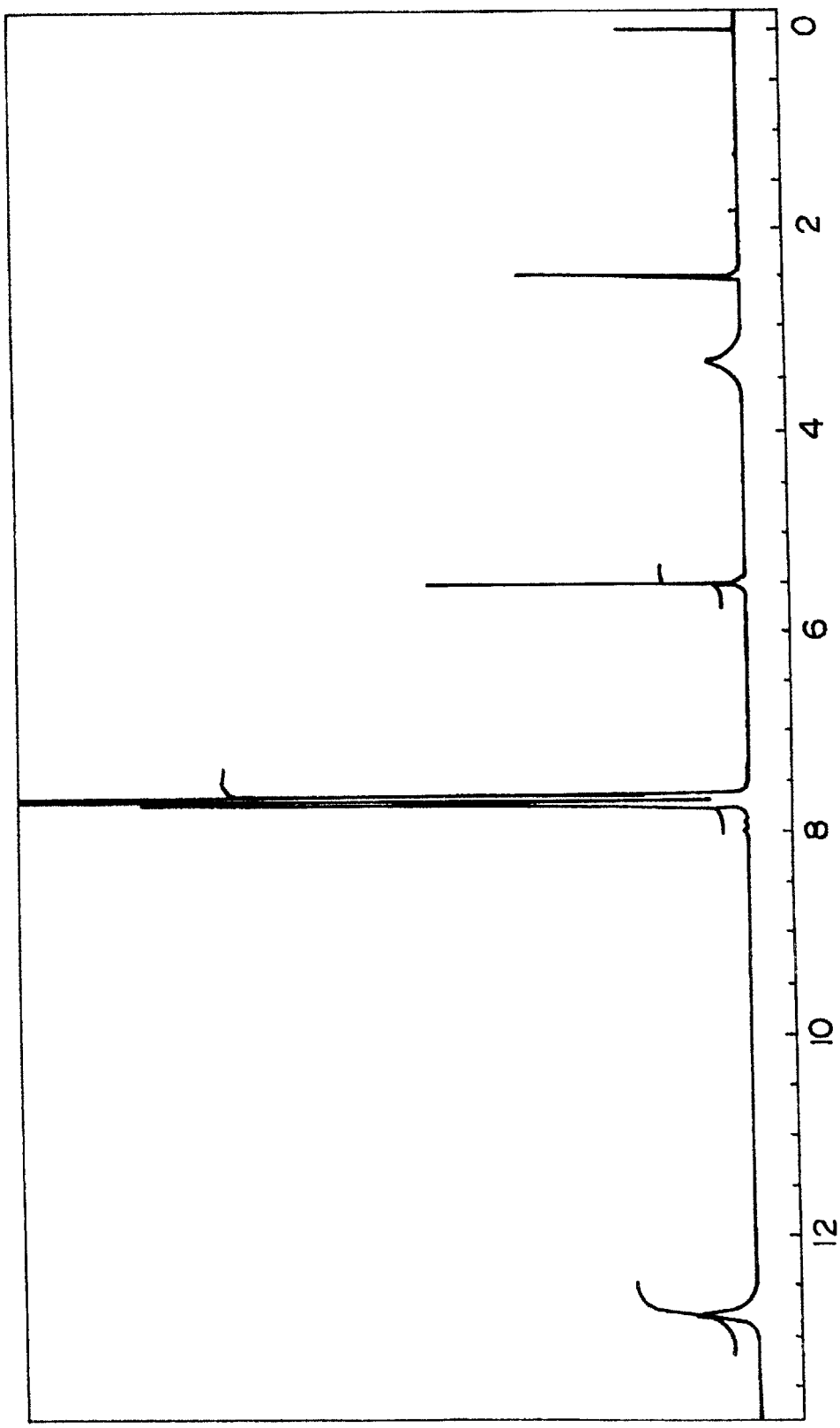
FIG. 1 shows a $^1$H-NMR spectrum (where dimethyl sulfoxide-$d_6$ was used as a solvent) of 1,1,2,2-tetrakis(4-carboxyphenyl)ethane of Example 1 of the present invention.

The present invention is described in reference to Examples. However, the present invention is not limited at all by these examples.

EXAMPLE 1

Synthesis of 1,1,2,2-Tetrakis(4-carboxyphenyl) ethane

Reaction Stage (1)

Into a 500-ml, four-neck flask with a stirring rod were placed 14.21 g (0.053 mol) of 1,1-bis(4-carboxyphenyl) ketone and a mixed solvent of 150 ml of 0.75M aqueous sodium hydroxide and 40 ml of methanol, and stirred to dissolve at room temperature. 2.11 g (0.053 mol) of sodium borohydride was added to the resulting solution and stirred at room temperature for 4.5 hours to complete the reaction. The reaction solution was adjusted to pH 3 with 6N hydrochloric acid. The precipitated solid was separated by filtration, and dried under vacuum at 50° C. to give 14.31 g of 1,1-bis(4-carboxyphenyl)methanol (yield: 95%).

Reaction Stage (2)

Into a 300-ml, four-neck flask with a stirring rod and a thermometer were placed 7.98 g (0.029 mol) of the 1,1-bis(4-carboxyphenyl)methanol obtained in Reaction Stage (1), 80 ml of acetic acid and 50.00 g (0.29 mol) of a 48% solution of hydrobromic acid, and stirred for 3 hours at 95 to 100° C. to complete the reaction. The reaction solution was left in the atmosphere to cool down to room temperature. The precipitated solid was separated by suction filtration, and dried under vacuum at 50° C. to give 6.59 g of 1,1-bis(4-carboxyphenyl)bromomethane (yield: 67%).

Reaction Stage (3)

Into a 200-ml, four-neck flask with a stirring rod and a thermometer were placed 6.50 g (0.019 mol) of the 1,1-bis (4-carboxyphenyl)bromomethane obtained in Reaction Stage (2) and 40 g of thionyl chloride, and gradually heated up with stirring to dissolve. The reaction solution was stirred at reflux for 2 hours to complete the reaction. Thionyl chloride was distilled off under reduced pressure to give an orange-colored oil. 125 ml of ethanol was added to the oil and further 4.55 g (0.058 mol) of pyridine was added to stir at room temperature for 17 hours for the completion of the reaction. The reaction solvent was distilled off. The residue was dissolved in 120 ml of ethyl acetate. The obtained solution was washed with 70 ml of water three times to remove pyridinium chloride produced in the reaction. The ethyl-acetate layer was dried over anhydrous sodium sulfate. Ethyl acetate was distilled off to give 6.53 g of 1,1-bis(4-carboxyphenyl)bromomethane diethyl ester (yield: 84%).

Reaction Stage (4) Into a 100-ml, three-neck flask with a stirring rod and a reflux condenser equipped with a $CaCl_2$ tube were placed 6.30 g (0.016 mol) of the 1,1-bis(4-carboxyphenyl)bromomethane diethyl ester obtained in Reaction Stage (3), 30 ml of dehydrated ethyl acetate and 1.26 g (0.026 mol) of zinc dust, and were dissolved by heating up to reflux with stirring. The resulting solution was further stirred at reflux for 6.5 hours to complete the reaction. The reaction solution was left in the atmosphere to cool down to room temperature 90 ml of ethyl acetate and 45 ml of ethanol were added to dissolve zinc bromide produced in the reaction system. Insoluble matter was filtered off 500 ml of acetone was added to the filtrate, and heated to around 50° C. with stirring. Then the excessive zinc dust was filtered off. The filtrate was concentrated. The obtained white powder was washed with 50% aqueous ethanol to remove zinc bromide completely from the powder, and dried under vacuum at 50° C. to give 3.21 g of 1,1,2,2-tetrakis(4-carboxyphenyl)ethane tetraethyl ester (yield: 64%).

Reaction Stage (5)

Into a 1-L, three-neck flask with a stirring rod were placed 3.10 g (5 mmol) of the 1,1,2,2-tetrakis(4-carboxylatephenyl) ethane tetraethyl ester obtained in Reaction Stage (4) and 430 ml of acetone, and stirred to dissolve. Into the resulting solution was added 40 ml (40 mmol) of 1N aqueous sodium hydroxide to stir at room temperature. Acetone was being distilled off as the substrate was disappearing. 20 ml of 1N aqueous sodium hydroxide was further added to accelerate the reaction. Acetone was almost distilled off finally and the reaction system was stirred in 1N aqueous sodium hydroxide. The reaction was terminated 55 hours after the beginning of stirring. The reaction solution was adjusted to pH 3 with 6N hydrochloric acid. The precipitated solid was separated by filtration, and dried under vacuum at 50° C. to give 2.44 g of white powder (yield: 96%).

Figure 2:
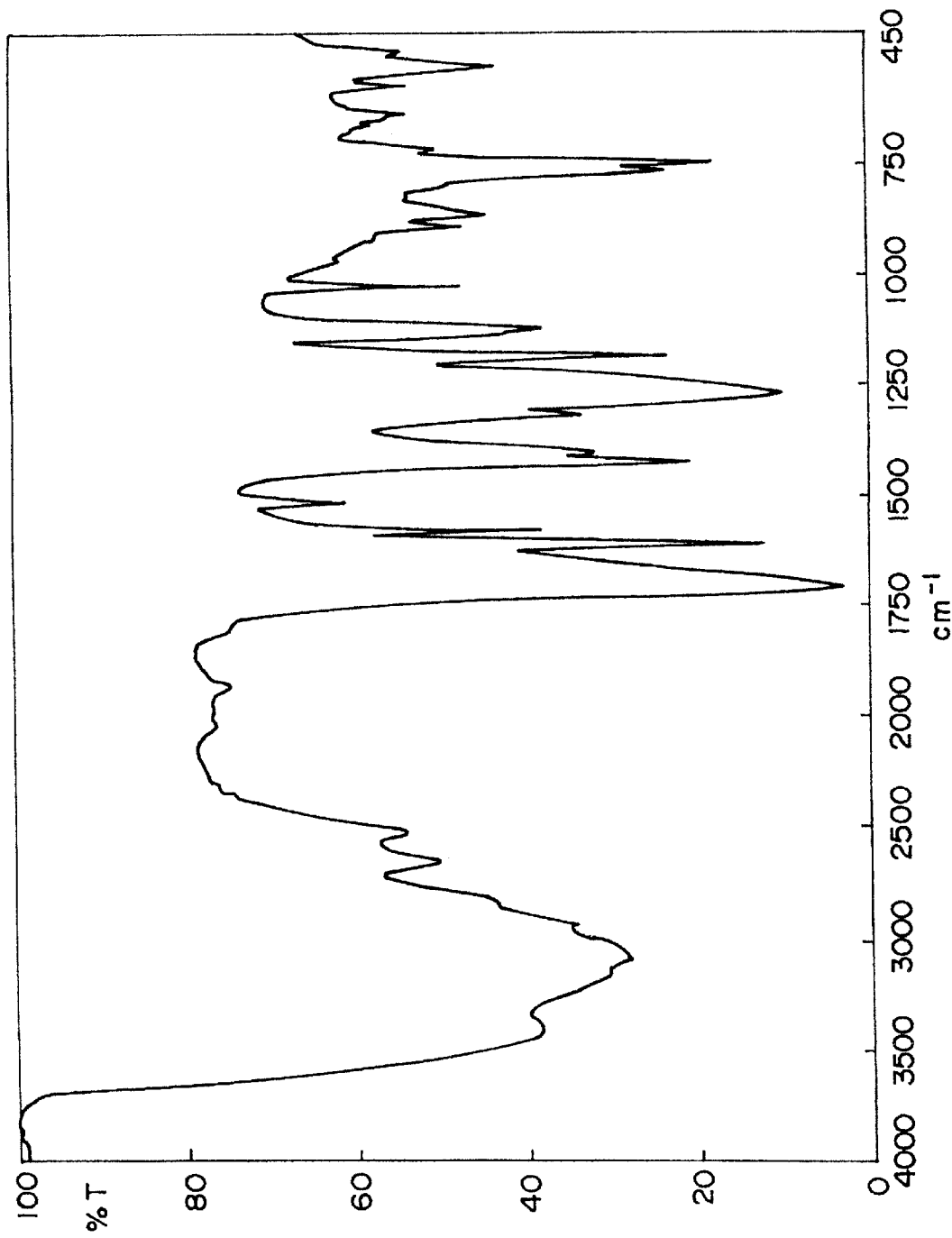
FIG. 2 shows an IR spectrum (KBr) of 1,1,2,2-tetrakis(4-carboxyphenyl)ethane of Example 1 of the present invention.

It was confirmed by NMR and IR spectra that the obtained was 1,1,2,2-tetrakis(4-carboxyphenyl)ethane. The absorption by the carboxyl group in the IR spectra was seen in the region of the wave numbers of the absorption by the carboxyl groups of ordinary associated aromatic carboxylic acids. It suggested that 1,1,2,2-tetrakis(4-carboxyphenyl) ethane existed as an intramolecular association. The melting point calculated by the top peak method in DSC (Differential Scanning Calorimetry) was as high as 386° C., reflecting the association condition. It was therefore understood that the heat stability was very good. A $^1$H-NMR spectrum (where dimethyl sulfoxide-$d_6$ was used as a solvent) and IR spectrum (KBr) of the obtained 1,1,2,2-tetrakis(4-carboxyphenyl)ethane are shown in FIGS. 1 and 2, respectively.

EXAMPLE 2

Preparation of Molecular Compounds Containing 1,1,2,2-Tetrakis(4-carboxyphenyl)ethane as a Constituent Compound (No. 1)

0.25 mmol (0. 13 g) of 1,1,2,2-tetrakis(4-carboxyphenyl)ethane was heated to dissolve in 3 ml of pyridine, and left to stand at room temperature for 24 hours. The precipitated crystals were separated by filtration, and dried under reduced pressure using a rotary vacuum pump at 40° C. for an hour to give a molecular compound consisting of 1,1,2,2-tetrakis(4-carboxyphenyl)ethane and pyridine of a composition ratio of 1:3 (mole ratio). The same procedure was repeated except that N,N-dimethylformamide was used instead of pyridine. After the solution was left to stand for 24 hours at room temperature, N,N-dimethylformamide was distilled under reduced pressure. The residue was further dried under reduced pressure using a rotary vacuum pump at 80° C. for an hour, to give a molecular compound composing 1,1,2,2-tetrakis(4-carboxyphenyl)ethane and N,N-dimethylformamide of a composition ratio of 1:1 (mole ratio). It was confirmed by thermal analyses (TG/DTA), $^1$H-NMR and X-ray diffraction patterns that each of the obtained compounds was a molecular compound of the said composition ratio. It was also confirmed from the X-ray diffraction patterns that each of the molecular compounds was obviously crystalline.

Figure 3:
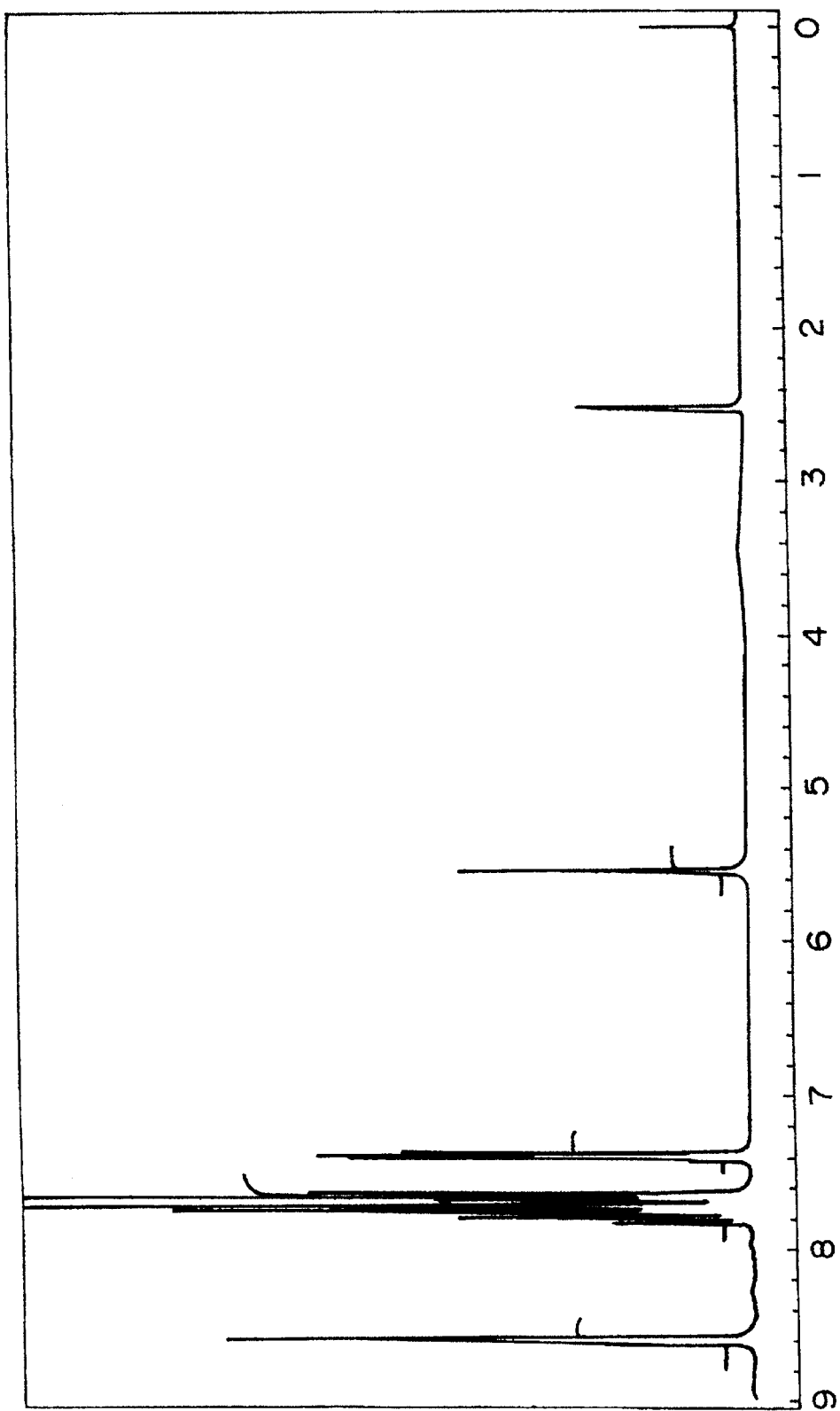
FIG. 3 shows a $^1$H-NMR spectrum (where dimethyl sulfoxide-$d_6$ was used as a solvent) of the clathrate compound composing 1,1,2,2-tetrakis(4-carboxyphenyl)ethane and pyridine of a composition ratio of 1:3 (mole ratio), of Example 2 of the present invention.
Figure 4:
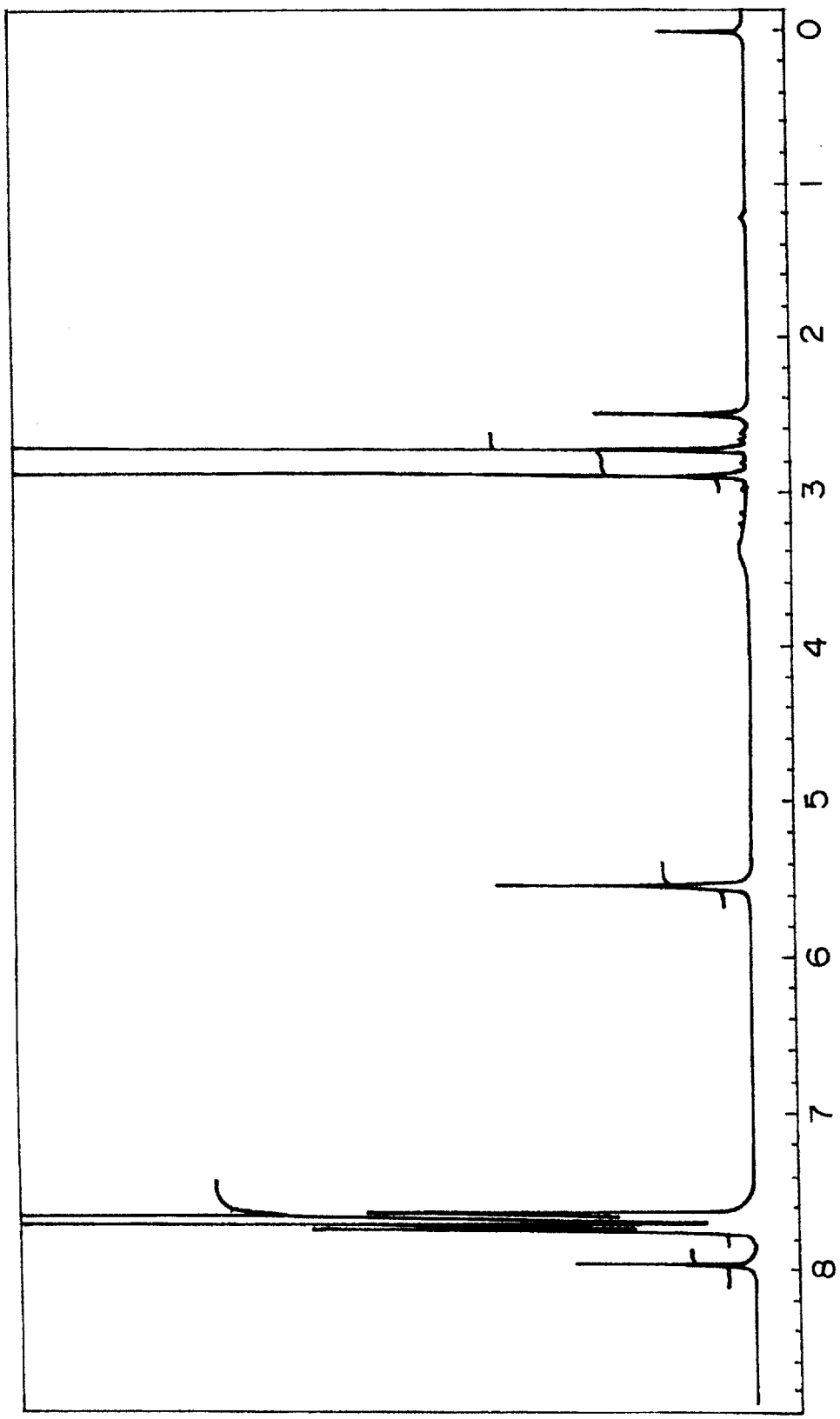
FIG. 4 shows a $^1$H-NMR spectrum (where dimethyl sulfoxide-$d_6$ was used as a solvent) of the clathrate compound composing 1,1,2,2-tetrakis(4-carboxyphenyl)ethane and N,N-dimethylformamide of a composition ratio of 1:1 (mole ratio), of Example 2 of the present invention.
Figure 5:
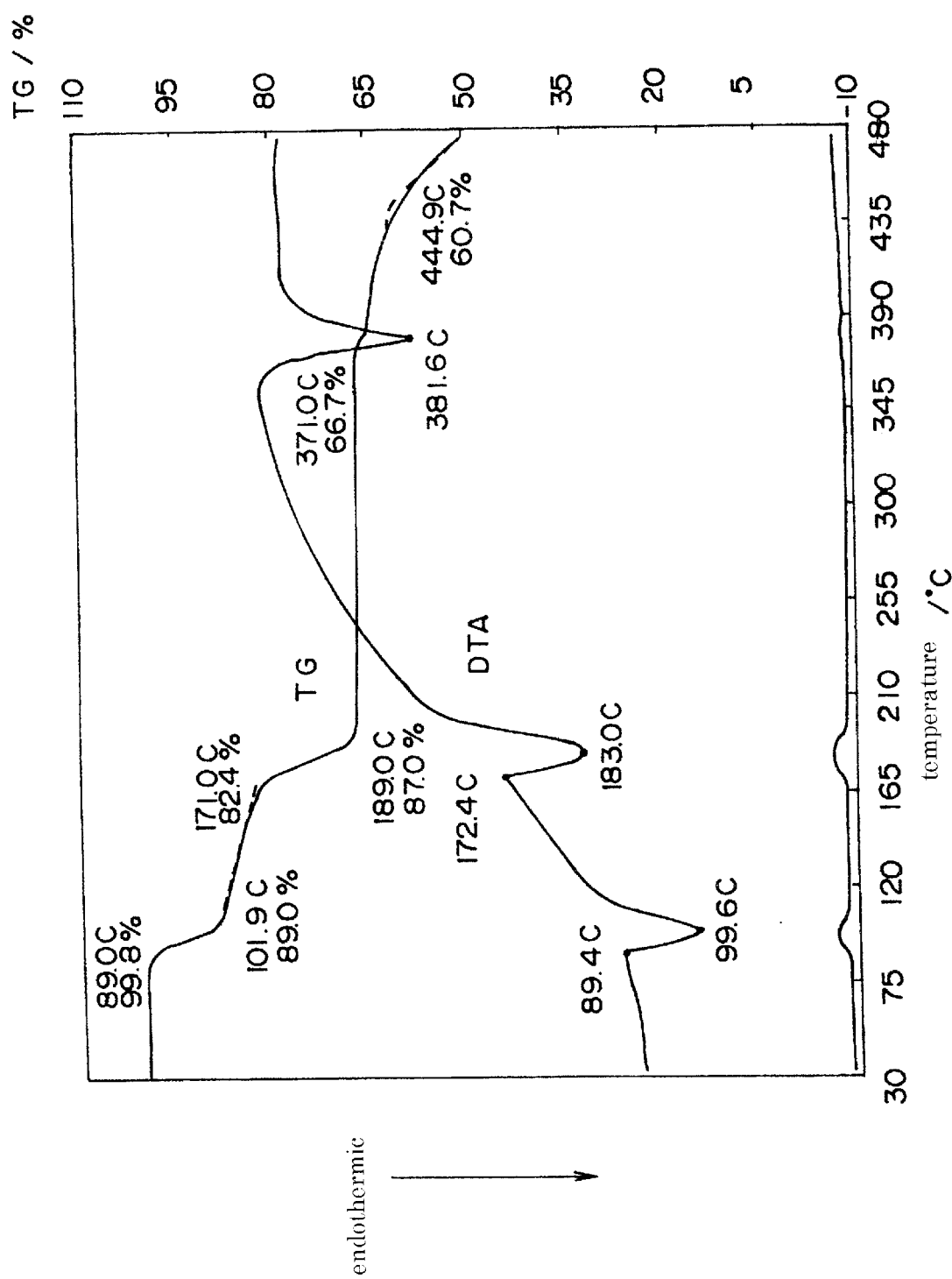
FIG. 5 shows a thermal analysis (TG/DTA) chart of the clathrate compound composing 1,1,2,2-tetrakis(4-carboxyphenyl)ethane and pyridine of a composition ratio of 1:3 (mole ratio), of Example 2 of the present invention.
Figure 6:
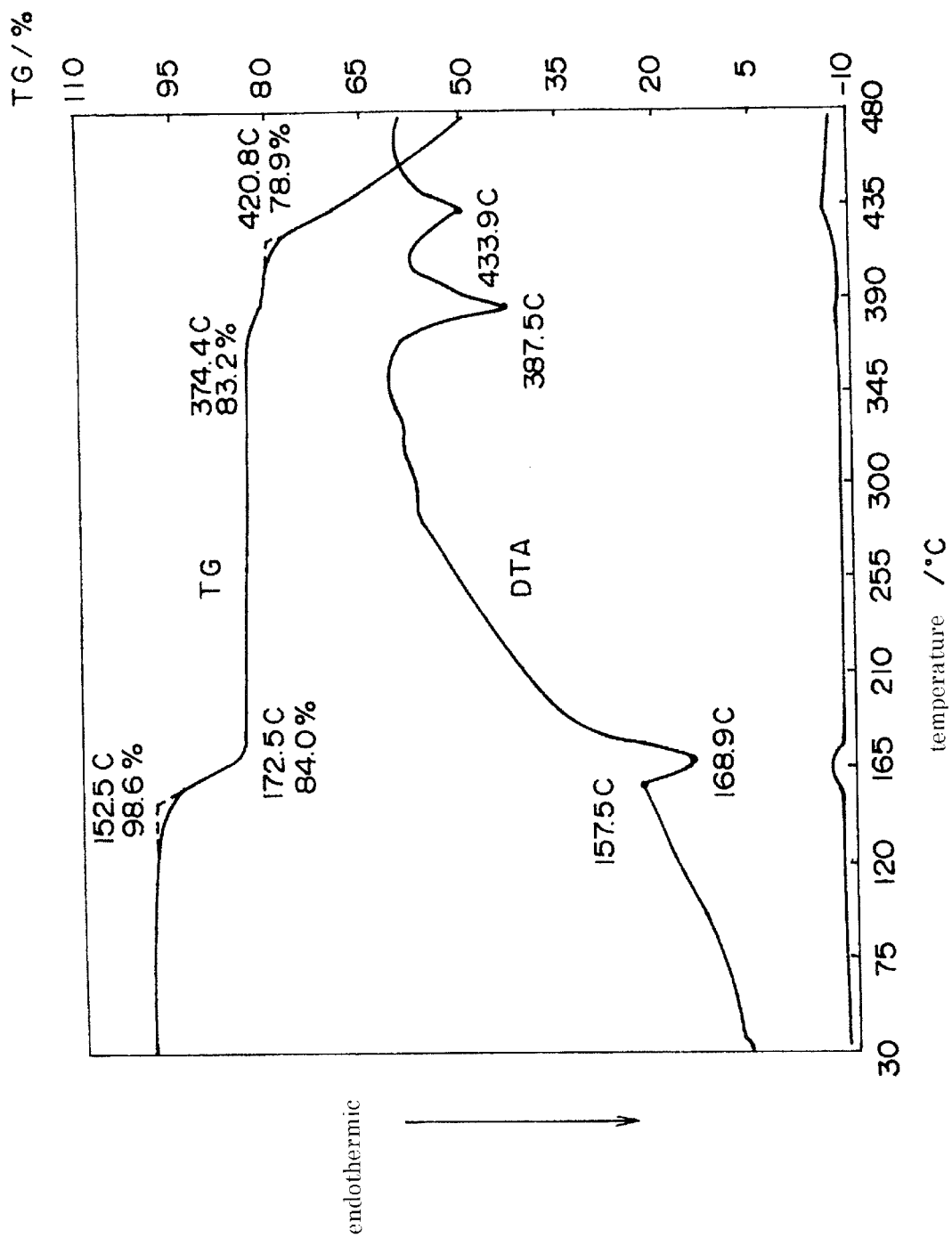
FIG. 6 shows a thermal analysis (TG/DTA) chart of the clathrate compound composing 1,1,2,2-tetrakis(4-carboxyphenyl)ethane and N,N-dimethylformamide of a composition ratio of 1:1 (mole ratio), of Example 2 of the present invention.
Figure 7:
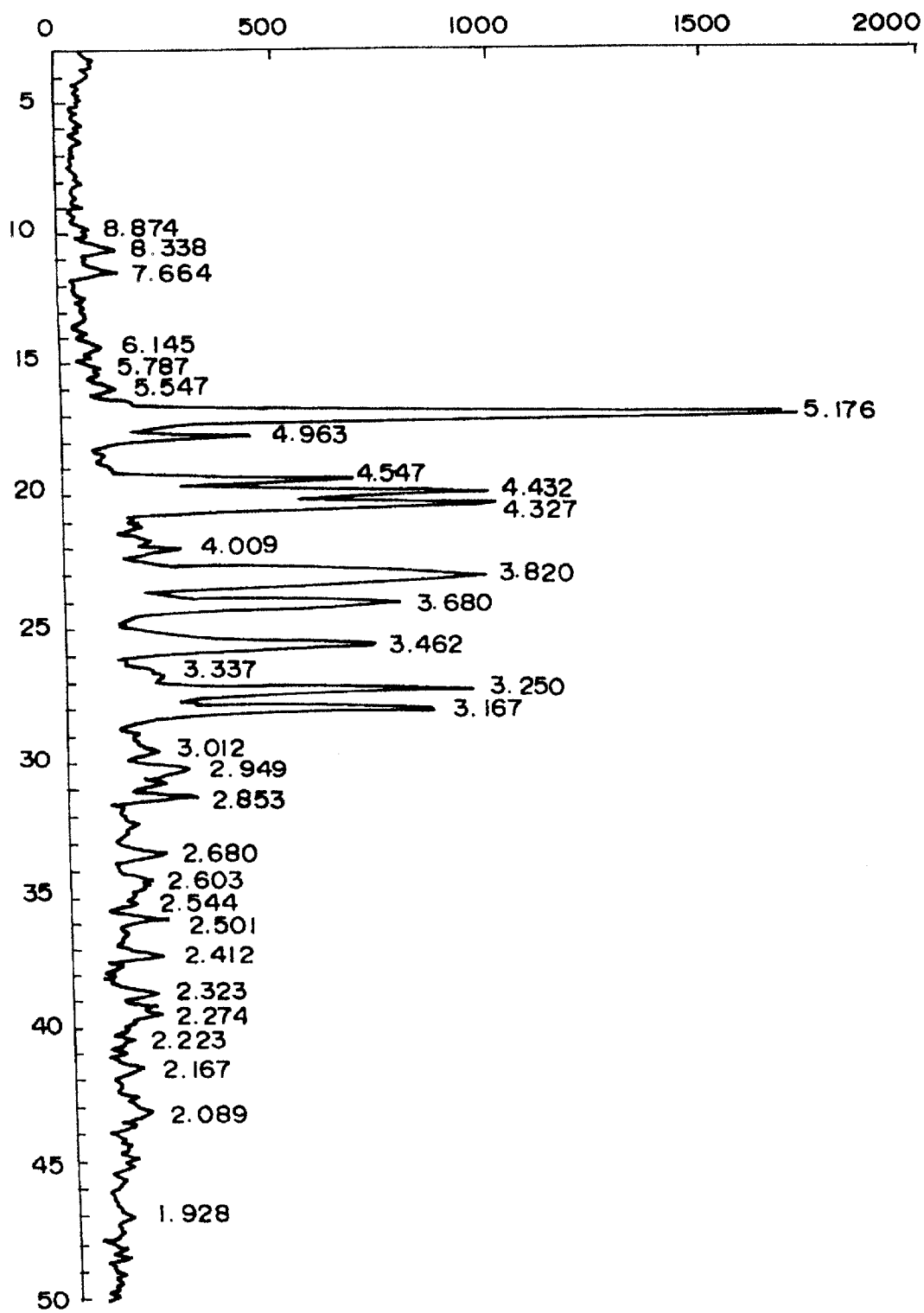
FIG. 7 shows a powder X-ray diffraction pattern of the clathrate compound composing 1,1,2,2-tetrakis(4-carboxyphenyl)ethane and pyridine of a composition ratio of 1:3 (mole ratio), of Example 2 of the present invention.
Figure 8:
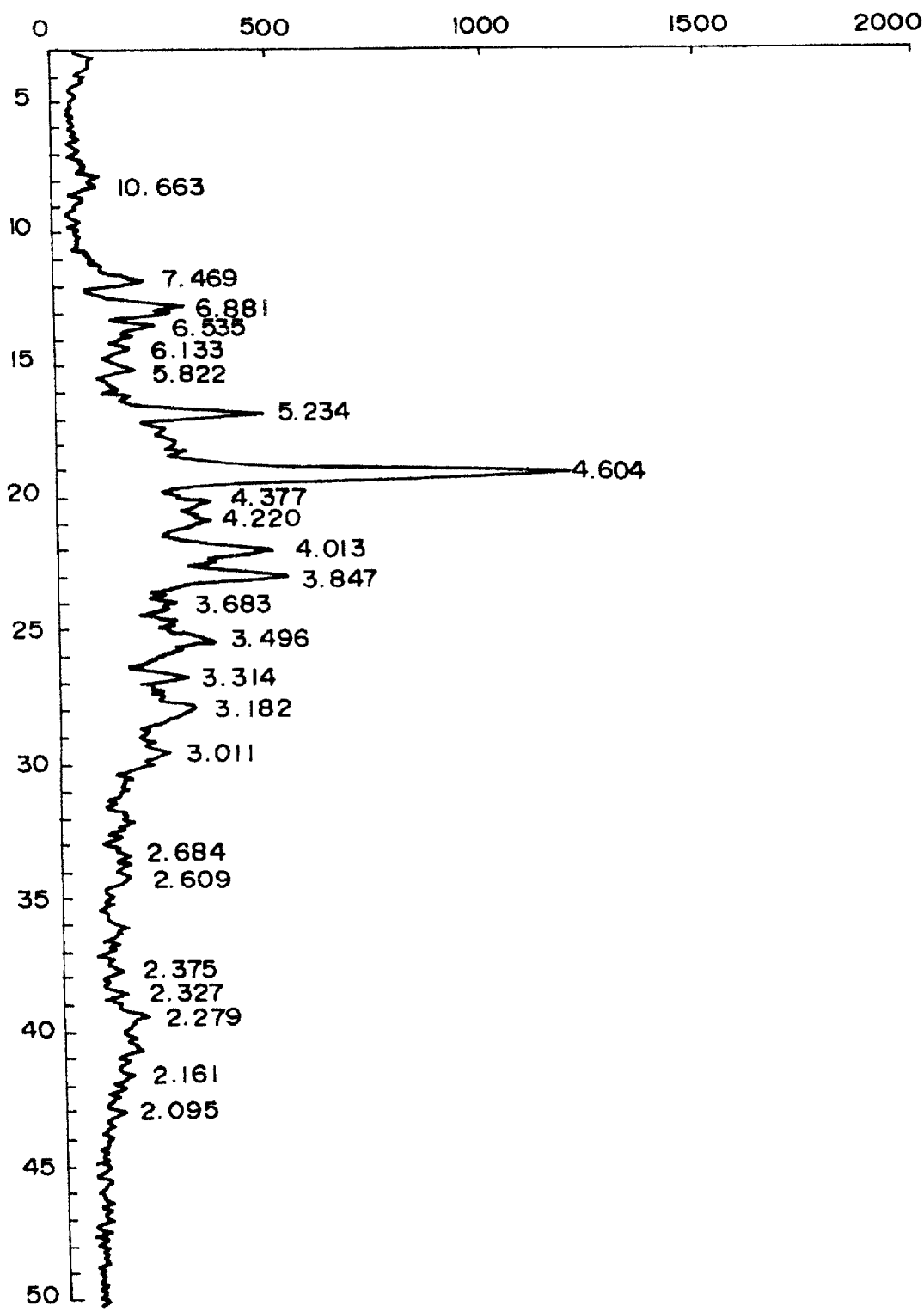
FIG. 8 shows a powder X-ray diffraction pattern of the clathrate compound composing 1,1,2,2-tetrakis(4-carboxyphenyl)ethane and N,N-dimethylformamide of a composition ratio of 1:1 (mole ratio), of Example 2 of the present invention.
Figure 9:
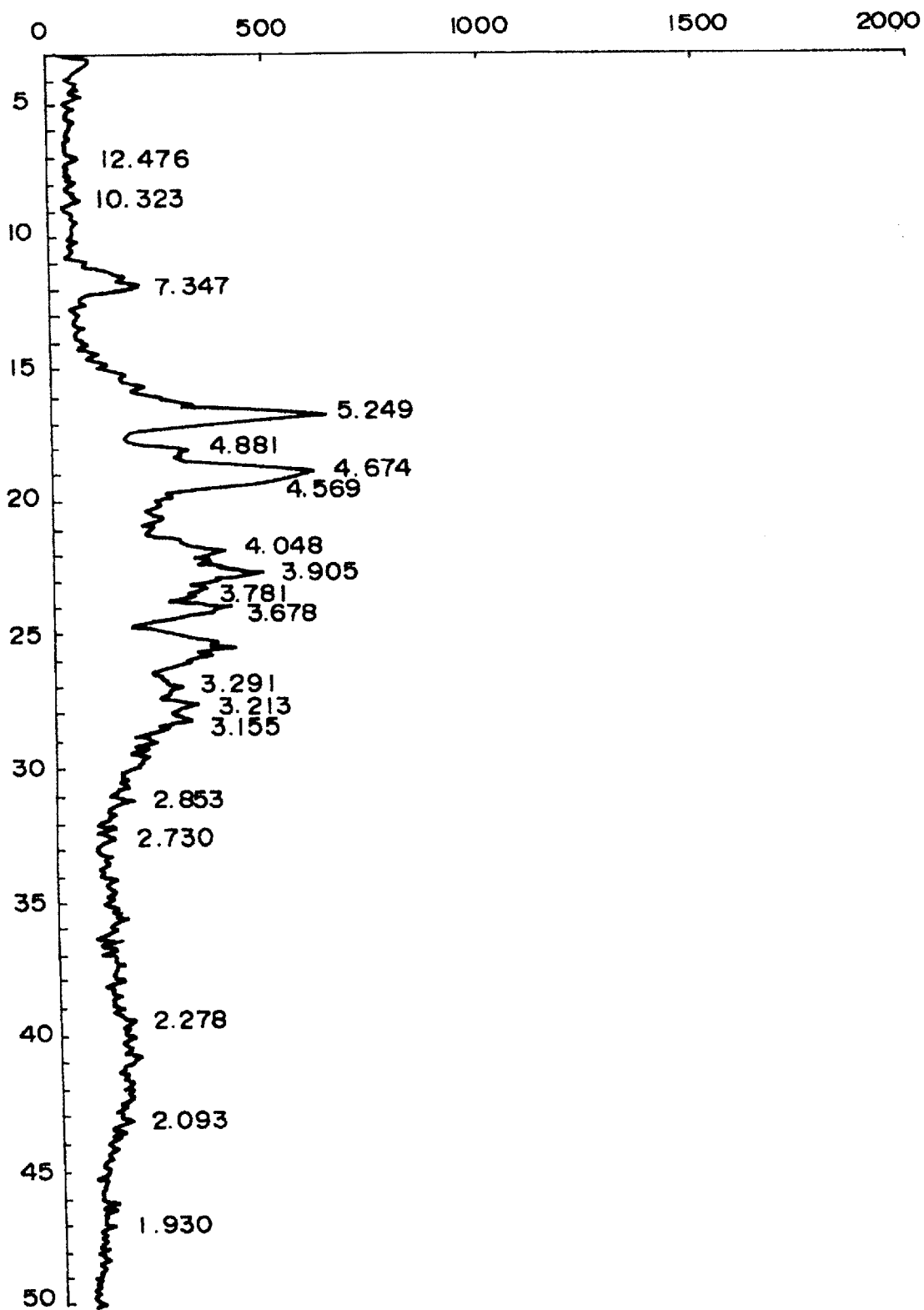
FIG. 9 shows a powder X-ray diffraction pattern of 1,1,2,2-tetrakis(4-carboxyphenyl)ethane of Example 1 of the present invention.

Each of the molecular compounds released pyridine in the range of about 89° C. and 189° C., and N,N-dimethylformamide between about 153° C. and 173° C., respectively. $^1$H-NMR spectra (where dimethyl sulfoxide-$d_6$ was used as a solvent) of the molecular compounds of 1,1,2,2-tetrakis(4-carboxyphenyl)ethane with pyridine and with N,N-dimethylformamide are shown in FIGS. 3 and 4, respectively. Their thermal analysis (TG/DTA) charts are shown in FIGS. 5 and 6, respectively. Powder X-ray diffraction patterns of the molecular compounds composing 1,1,2,2-tetrakis(4-carboxyphenyl)ethane with pyridine and with N,N-dimethylformamide are shown in FIGS. 7 and 8, respectively. For comparison, a powder X-ray diffraction pattern of 1,1,2,2-tetrakis(4-carboxyphenyl)ethane is shown in FIG. 9. As described above, the molecular compounds of the present invention have made it possible to powder pyridine and N,N-dimethylformamide, which are liquids at room temperature, and to control the volatility.

EXAMPLE 3

Preparation of Molecular Compounds Containing 1,1,2,2-Tetrakis(4-carboxyphenyl)ethane as a Constituent Compound (No. 2)

0.196 mmol (0.1 g) of 1,1,2,2-tetrakis(4-carboxyphenyl)ethane was suspended in 5 ml of 1,4-dioxane, heated at reflux for 10 minutes, and left to stand at room temperature for 24 hours. The solid component was separated by filtration, and dried under reduced pressure using a rotary vacuum pump at 40° C. for 2 hour to give a molecular compound consisting of 1,1,2,2-tetrakis(4-carboxyphenyl)ethane and 1,4-dioxane of a composition ratio of 1:1 (mole ratio). It was confirmed by thermal analyses (TG/DTA), $^1$H-NMR and X-ray diffraction patterns that the obtained compound was a molecular compound of the said composition ratio. It was also confirmed from the X-ray diffraction patterns that the molecular compound was obviously crystalline.

Figure 10:
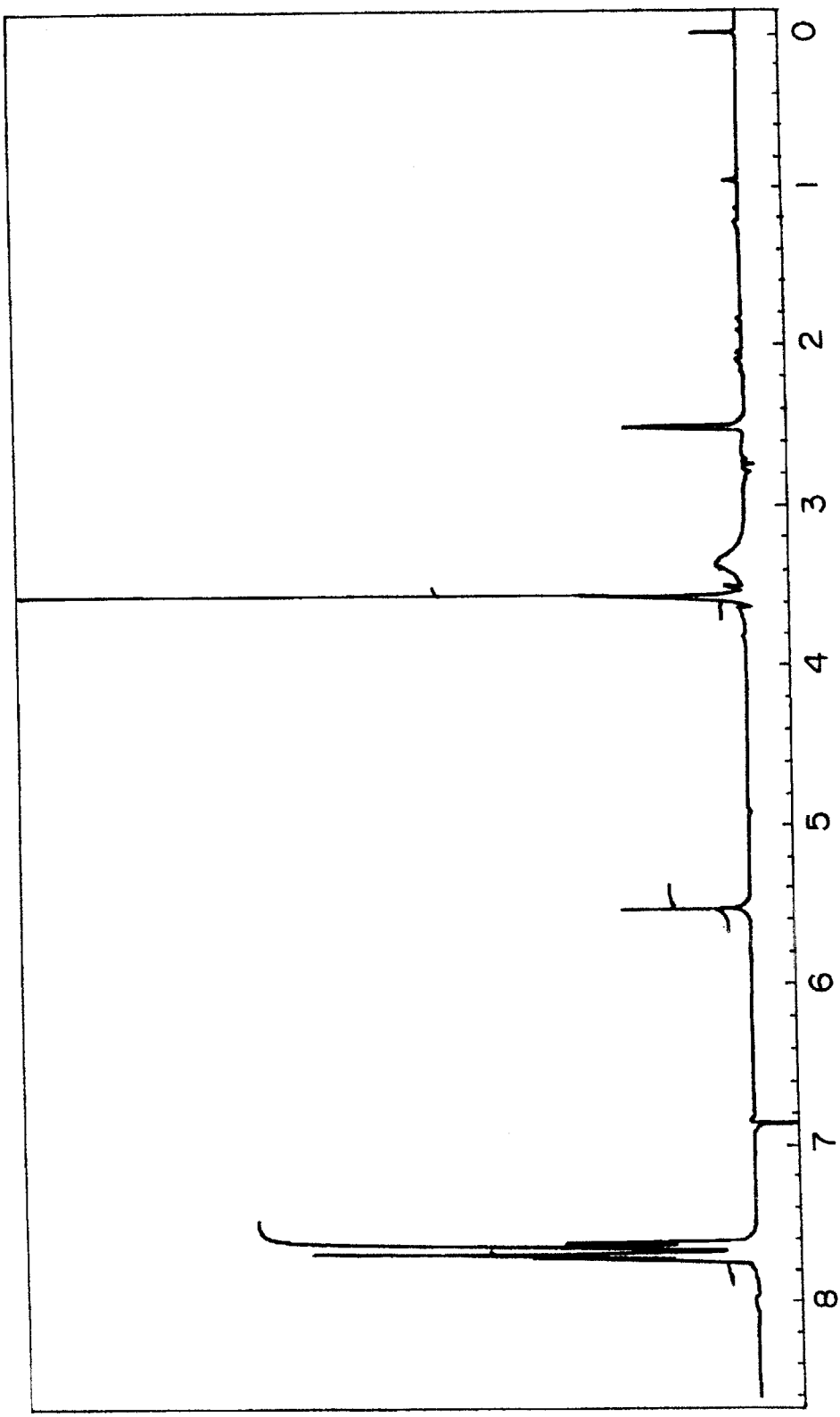
FIG. 10 shows a $^1$H-NMR spectrum (where dimethyl sulfoxide-$d_6$ was used as a solvent) of the clathrate compound composing 1,1,2,2-tetrakis(4-carboxyphenyl)ethane and 1,4-dioxane of a composition ratio of 1:1 (mole ratio), of Example 3 of the present invention.
Figure 11:
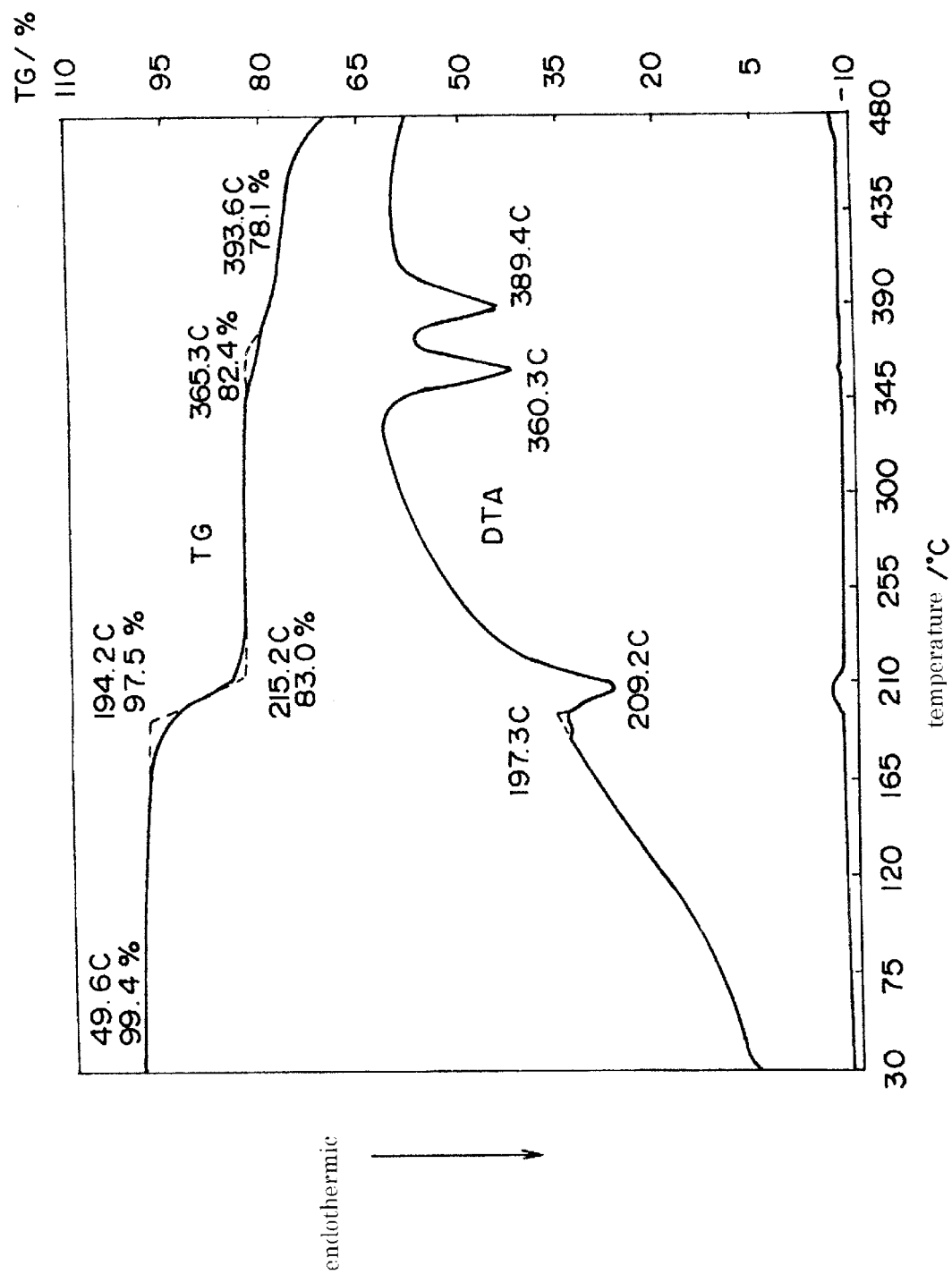
FIG. 11 shows a thermal analysis (TG/DTA) chart of the clathrate compound composing 1,1,2,2-tetrakis(4-carboxyphenyl)ethane and 1,4-dioxane of a composition ratio of 1:1 (mole ratio), of Example 3 of the present invention.
Figure 12:
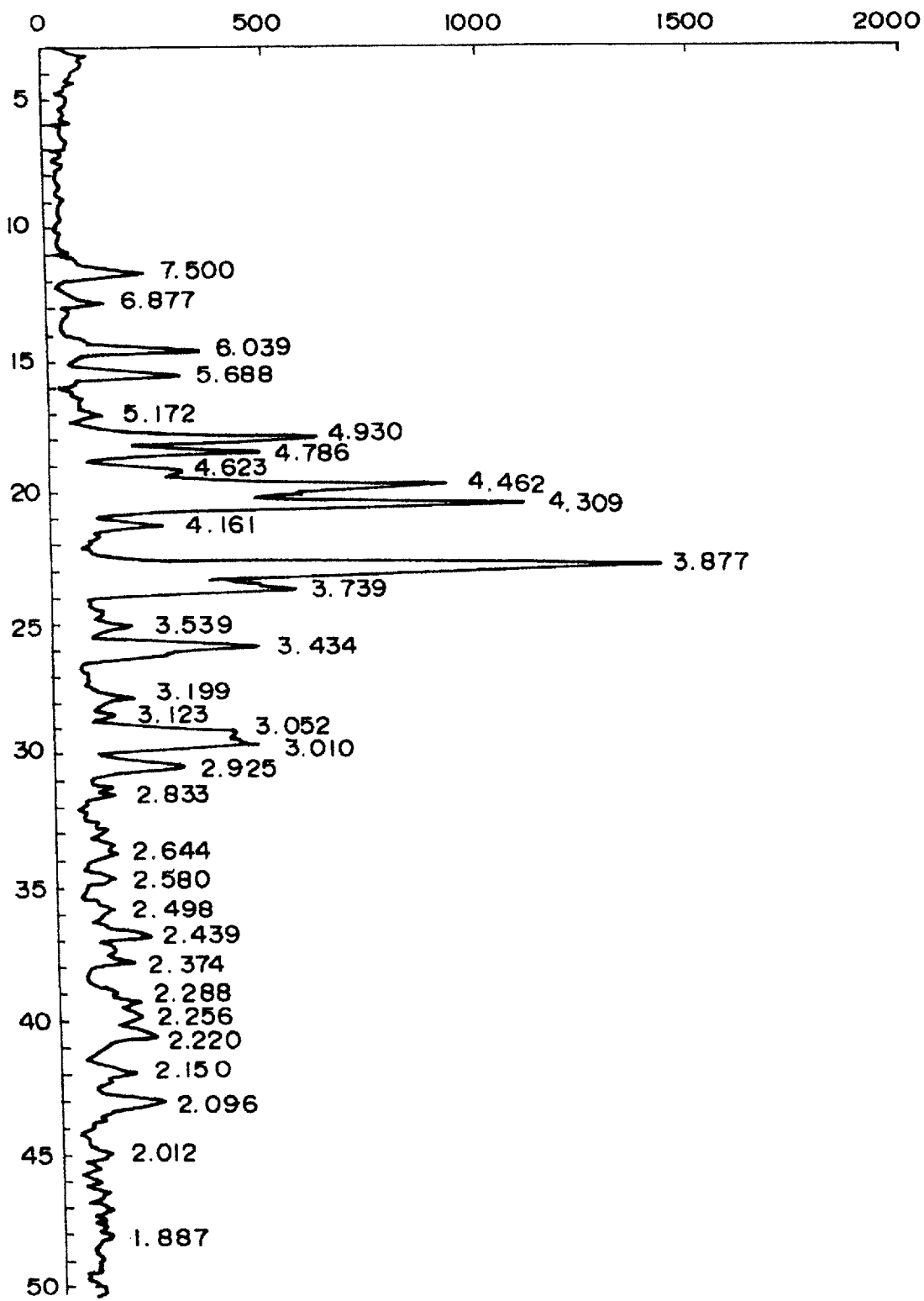
FIG. 12 shows a powder X-ray diffraction pattern of the clathrate compound composing 1,1,2,2-tetrakis(4-carboxyphenyl)ethane and 1,4-dioxane of a composition ratio of 1:1 (mole ratio), of Example 3 of the present invention.

The molecular compound released 1,4-dioxane in the range of about 194° C. and 215° C. A $^1$H-NMR spectrum (where dimethyl sulfoxide-$d_6$ was used as a solvent) and a thermal analysis (TG/DTA) chart of the molecular compound of 1,1,2,2-tetrakis(4-carboxyphenyl)ethane and 1,4-dioxane are shown in FIGS. 10 and 11, respectively. A powder X-ray diffraction pattern of the molecular compound composing 1,1,2,2-tetrakis(4-carboxyphenyl)ethane and 1,4-dioxane is shown in FIG. 12. As described above, the molecular compound of the present invention has made it possible to powder 1,4-dioxane, which is a liquid at room temperature, and to control the volatility. Furthermore, the molecular compound of the present invention has become extremely stable against heat, as a known molecular compound consisting of 1,1,2,2-tetrakis(4-hydroxyphenyl)ethane, one of tetrakisphenols having divergent hydrogen bonding sites, and 1,4-dioxane releases 1,4-dioxane in a temperature range between about 96° C. and 115° C.

EXAMPLE 4

Preparation of Coordination Compounds of 1,1,2,2-Tetrakis(4-carboxyphenyl)ethane with Copper and With Zinc 770 mg (1.5 mmol) of 1,1,2,2-tetrakis(4-carboxyphenyl)ethane was dissolved in 10 ml of 1N aqueous sodium hydroxide. Ethyl alcohol was gradually added to the resulting solution. The precipitated white solid was separated by filtration, and dried under vacuum at 50° C. to give 799 mg of 1,1,2,2-tetrakis(4-carboxyphenyl)ethane tetrasodium salt as powder (yield: 88%). 100 mg (0.17 mmol) of the white powder was dissolved in 4 ml of distilled water, and mixed with 4 ml of an aqueous solution of 72 mg (0.42 mmol) of copper (II) chloride dihydrate dissolved. The mixed solution was stirred with a magnetic stirrer at room temperature for 30 minutes, and further left to stand at room temperature for 15 hours. The precipitated solid was separated by filtration, and dried under vacuum at 50° C. to give a coordination compound composing 1,1,2,2-tetrakis(4-carboxyphenyl)ethane, bivalent copper ion and water of a composition ratio of about 1:3:6 (mole ratio). The same procedure was repeated, except that 57 mg (0.42 mmol) of zinc chloride was used instead of copper (II) chloride dihydrate, to give a coordination compound composing 1,1,2,2-tetrakis(4-carboxyphenyl)ethane, bivalent zinc ion and water of a composition ratio of about 1:2:7 (mole ratio).

Figure 13:
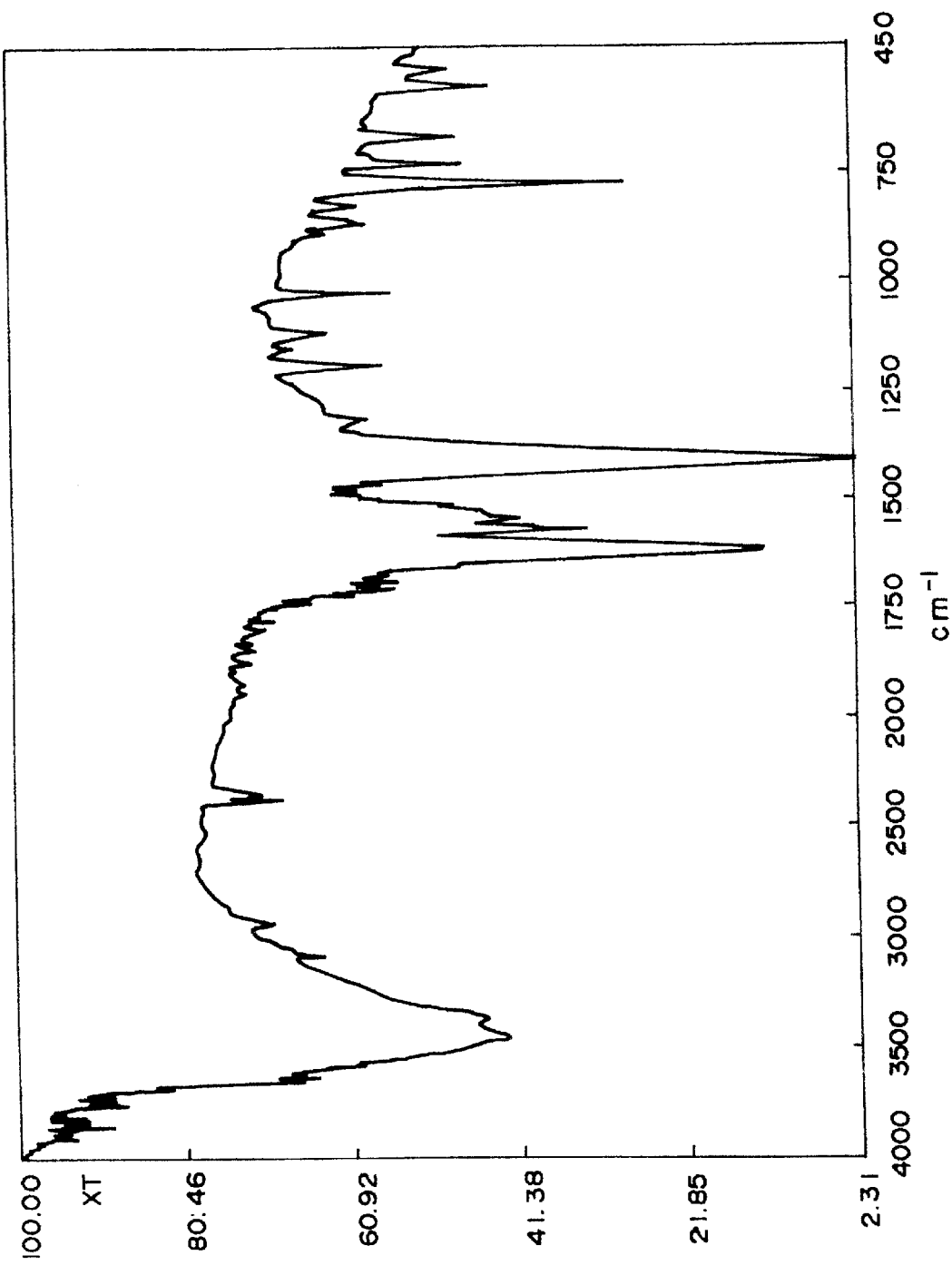
FIG. 13 shows an IR spectrum (KBr) of the coordination compound composing 1,1,2,2-tetrakis(4-carboxyphenyl) ethane and bivalent copper ion, of Example 4 of the present invention.
Figure 14:
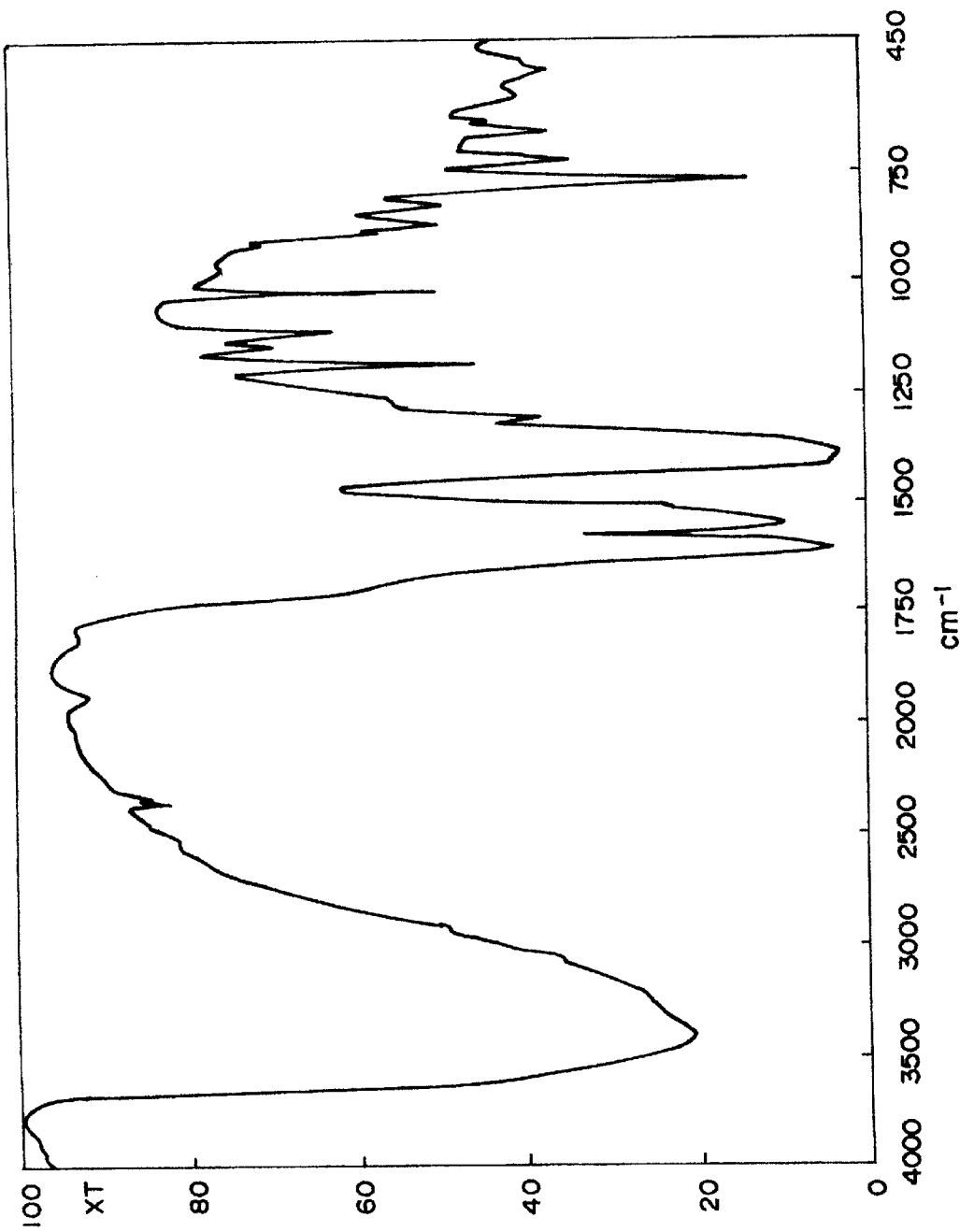
FIG. 14 shows an IR spectrum (KBr) of the coordination compound composing 1,1,2,2-tetrakis(4-carboxyphenyl) ethane and bivalent zinc ion, of Example 4 of the present invention.
Figure 15:
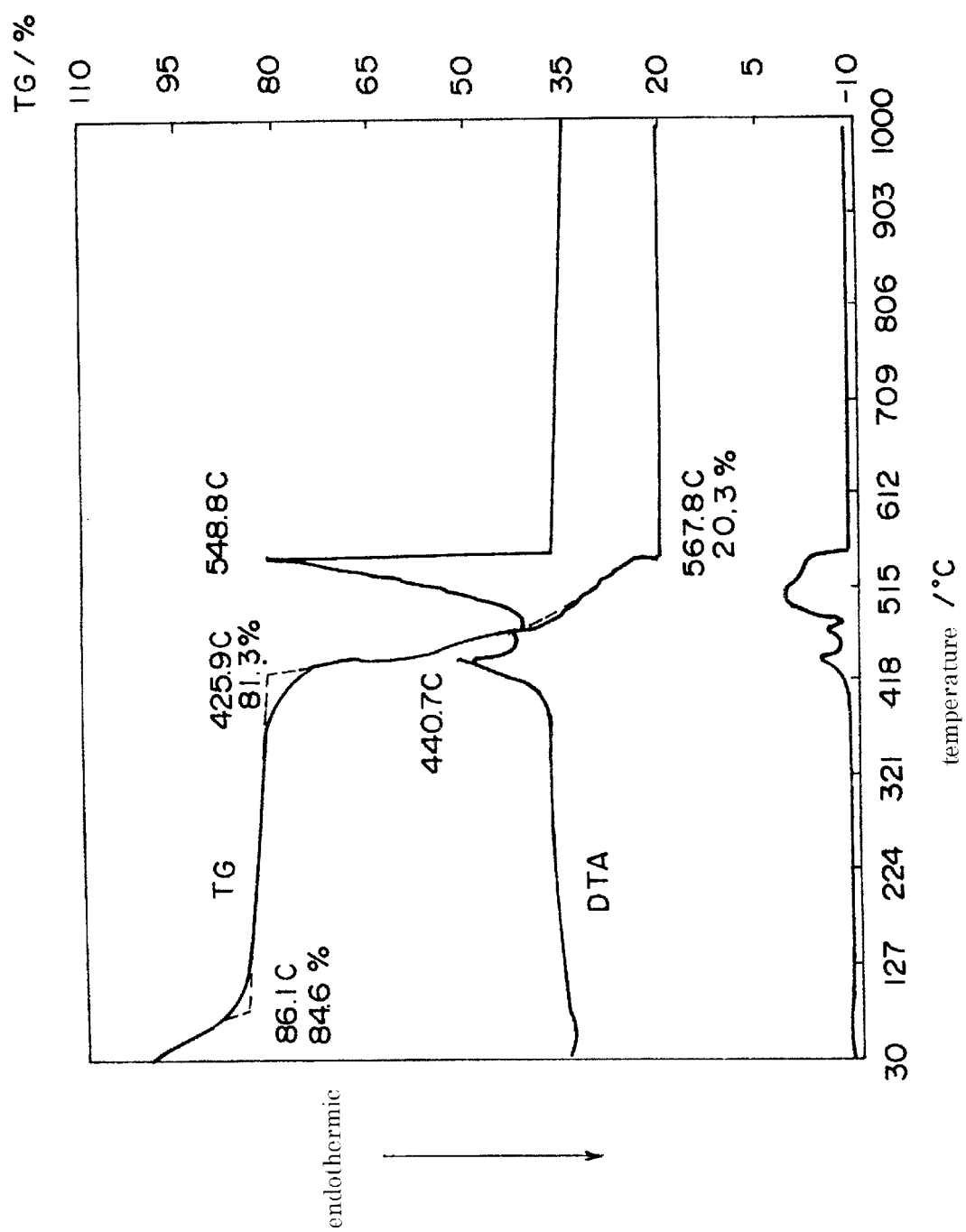
FIG. 15 shows a thermal analysis (TG/DTA) chart of the coordination compound composing 1,1,2,2-tetrakis(4-carboxyphenyl)ethane and bivalent copper ion, of Example 4 of the present invention.
Figure 16:
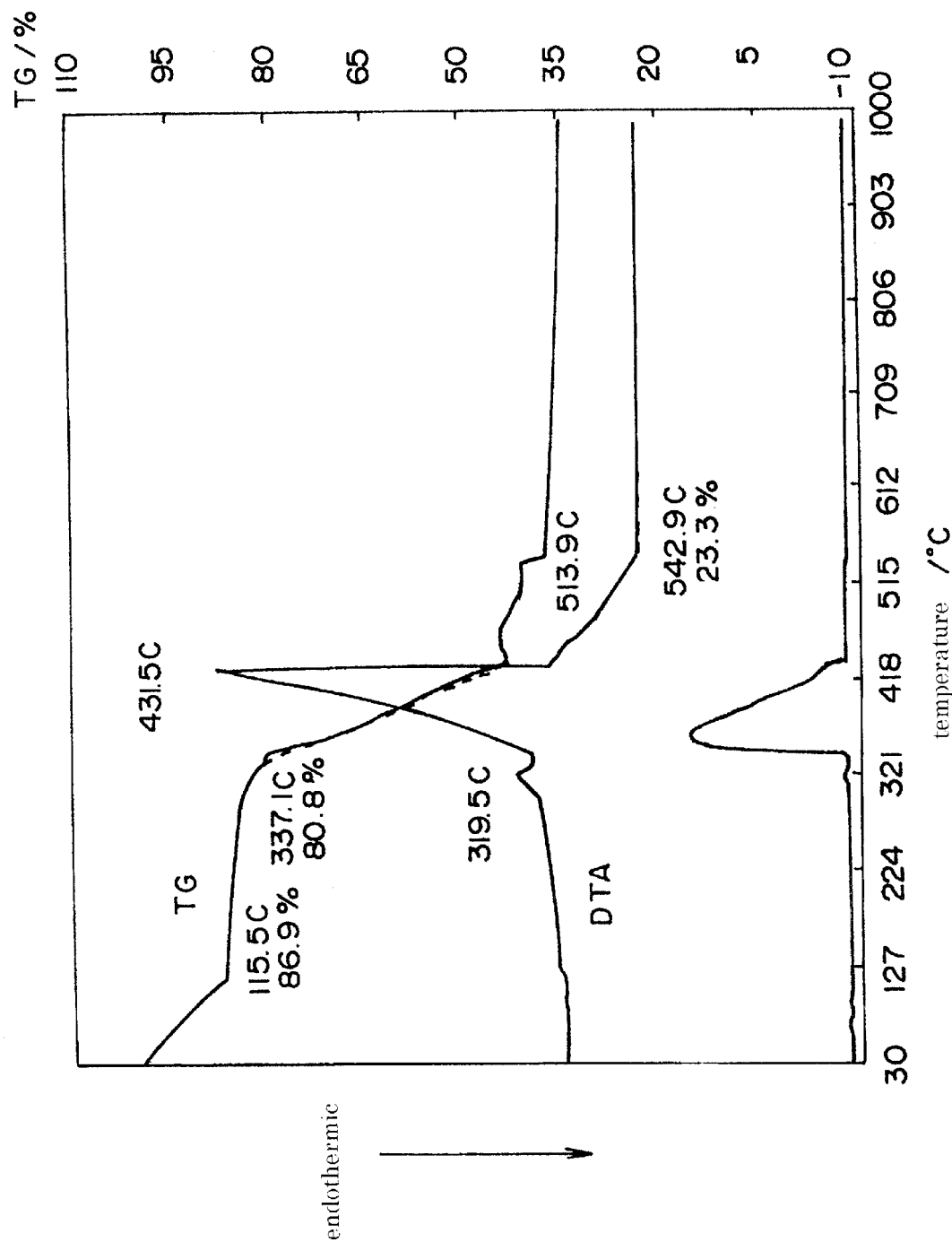
FIG. 16 shows a thermal analysis (TG/DTA) chart of the coordination compound composing 1,1,2,2-tetrakis(4-carboxyphenyl)ethane and bivalent zinc ion, of Example 4 of the present invention.

It was confirmed by a shift of the absorption by the carbonyl group and disappearance of the absorption by the hydroxy group in IR spectra that the obtained compounds were coordination compounds of 1,1,2,2-tetrakis(4-carboxyphenyl)ethane with copper and with zinc. That these compounds were coordination compounds of the said composition ratios was confirmed by atomic absorption analyses and thermal analyses (TG/DTA) measured in the atmosphere. IR spectra (KBr) of the obtained coordination compounds of 1,1,2,2-tetrakis(4-carboxyphenyl)ethane with copper and with zinc are shown in FIGS. 13 and 14, respectively. Their thermal analysis charts are shown in FIGS. 15 and 16, respectively.

Applicability in Industry

The molecular compounds of the present invention, containing novel carboxylic acid derivatives as constituent compounds can be prepared by simple operations, endow various substances with functions such as chemical stabilization, nonvolatilization, prolongation of release and powderization, and selectively separate and recover specific substances. In addition, the molecular compounds of the present invention may be used together with a variety of substances, and in various forms. Besides, the coordination compounds of the present invention, having the novel carboxylic acid derivatives as ligands are useful as solid catalysts. Therefore, the novel carboxylic acid derivatives of the present invention are applicable to very wide fields, and have great significance in industry.

What is claimed is:

1. A carboxylic acid derivative represented by Formula (I) or (II)

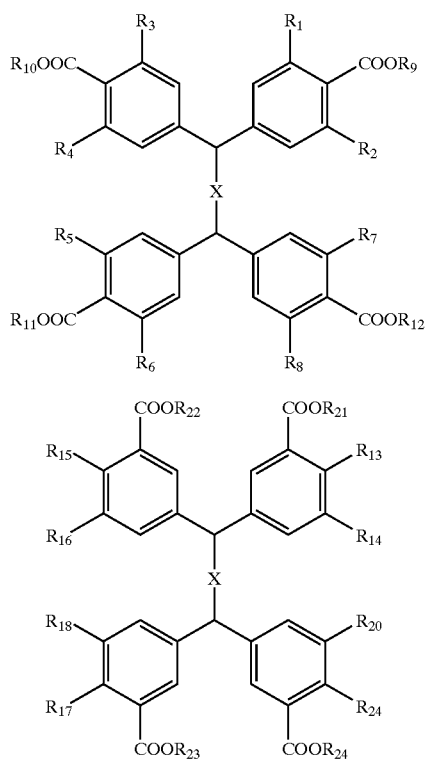

wherein, in Formulae (I) and (II), X is $(CH_2)_n$ or p-phenylene; n is 0, 1, 2 or 3; $R_1$ to $R_8$ and $R_{13}$ to $R_{20}$ are each hydrogen, $C_1$ to $C_6$ alkyl, $C_2$ to $C_4$ alkenyl, phenyl optionally substituted with $C_1$ to $C_6$ alkyl, halogen or $C_1$ to $C_6$ alkoxy; and $R_9$ to $R_{12}$ and $R_{21}$ to $R_{24}$ are each hydrogen, $C_1$ to $C_6$ alkyl, $C_2$ to $C_4$ alkenyl, $C_7$ to $C_{12}$ aralkyl or alkali metal.

2. A carboxylic acid derivative represented by Formula (III) or (IV) according to claim 1

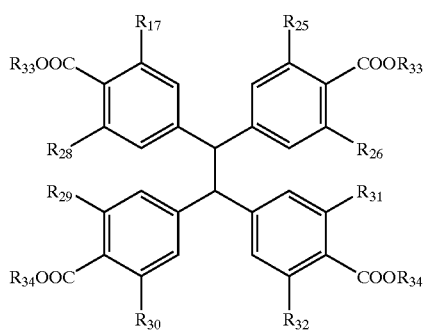

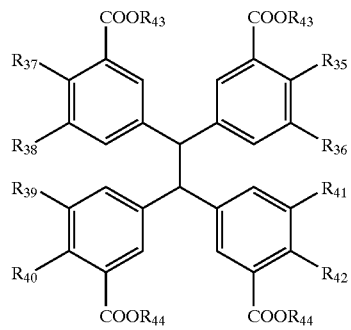

wherein, in Formulae (III) and (IV), $R_{25}$ to $R_{32}$ and $R_{35}$ to $R_{42}$ are each hydrogen, $C_1$ to $C_6$ alkyl, $C_2$ to $C_4$ alkenyl, phenyl optionally substituted with $C_1$ to $C_6$ alkyl, halogen or $C_1$ to $C_6$ alkoxy; and $R_{33}$, $R_{34}$, $R_{43}$ and $R_{44}$ are each hydrogen, $C_1$ to $C_6$ alkyl, $C_2$ to $C_4$ alkenyl, $C_7$ to $C_{12}$ aralkyl or alkali metal.

3. A process for the preparation of the carboxylic acid derivative represented by Formula (I) or (II) according to claim 1, characterized by the use of a 1,1-bis(3-carboxyphenyl)ketone derivative or 1,1-bis(4-carboxyphenyl)ketone derivative.

4. A molecular compound containing the carboxylic acid derivative of Formula (I) or (II) according to claim 1 as a constituent compound.

5. A molecular compound according to claim 4, in which the molecular compound is a clathrate compound.

6. A molecular compound according to claim 4 containing, as constituent compounds, the carboxylic acid derivative of Formula (I) or (II) according to claim 1, and an antibacterial agent, antifungal agent, insecticide, noxious insect repellent, perfume, deodorant, anti-fouling agent, curing agent and curing accelerator for coating agents, plastics and adhesives, natural essential oil, antioxidant, vulcanization accelerator or organic solvent that reacts with the said carboxylic acid derivative to form a molecular compound.

7. A molecular compound according to claim 5 containing, as constituent compounds, the carboxylic acid derivative of Formula (I) or (II) according to claim 1, and an antibacterial agent, antifungal agent, insecticide, noxious insect repellent, perfume, deodorant, anti-fouling agent, curing agent and curing accelerator for coating agents, plastics and adhesives, natural essential oil, antioxidant, vulcanization accelerator or organic solvent that reacts with the said carboxylic acid derivative to form a molecular compound.

8. A molecular compound according to claim 4, in which the carboxylic acid derivative of Formula (I) or (II) according to claim 1 is the carboxylic acid derivative of Formula (III) or (IV) according to claim 2.

9. A molecular compound according to claim 5, in which the carboxylic acid derivative of Formula (I) or (II) according to claim 1 is the carboxylic acid derivative of Formula (III) or (IV) according to claim 2.

10. A molecular compound according to claim 6, in which the carboxylic acid derivative of Formula (I) or (II) according to claim 1 is the carboxylic acid derivative of Formula (III) or (IV) according to claim 2.

11. A molecular compound according to claim 7, in which the carboxylic acid derivative of Formula (I) or (II) according to claim 1 is the carboxylic acid derivative of Formula (III) or (IV) according to claim 2.

12. A process for the preparation of the molecular compound according to claim 4, in which a carboxylic acid derivative is reacted with a constituent compound that reacts with the said carboxylic acid derivative to form a molecular compound.

13. A process for the preparation of the molecular compound according to claim 5, in which a carboxylic acid derivative is reacted with a constituent compound that reacts with the said carboxylic acid derivative to form a molecular compound.

14. A process for the preparation of the molecular compound according to claim 6, in which a carboxylic acid derivative is reacted with a constituent compound that reacts with the said carboxylic acid derivative to form a molecular compound.

15. A process for the preparation of the molecular compound according to claim 7, in which a carboxylic acid derivative is reacted with a constituent compound that reacts with the said carboxylic acid derivative to form a molecular compound.

16. A process for the preparation of the molecular compound according to claim 8, in which a carboxylic acid derivative is reacted with a constituent compound that reacts with the said carboxylic acid derivative to form a molecular compound.

17. A process for the preparation of the molecular compound according to claim 9, in which a carboxylic acid derivative is reacted with a constituent compound that reacts with the said carboxylic acid derivative to form a molecular compound.

18. A process for the preparation of the molecular compound according to claim 10, in which a carboxylic acid derivative is reacted with a constituent compound that reacts with the said carboxylic acid derivative to form a molecular compound.

19. A process for the preparation of the molecular compound according to claim 11, in which a carboxylic acid derivative is reacted with a constituent compound that reacts with the said carboxylic acid derivative to form a molecular compound.

* * * * *

UNITED STATES PATENT AND TRADEMARK OFFICE
CERTIFICATE OF CORRECTION

PATENT NO. : 6,566,548 B1  Page 1 of 1
DATED : May 20, 2003
INVENTOR(S) : Satoru Abe and Hiroshi Suzuki It is certified that error appears in the above-identified patent and that said Letters Patent is hereby corrected as shown below:

<u>Column 2,</u>
Line 43, replace "R24" with -- R19 --.
Line 55, replace "R17" with -- R27 --.

<u>Column 10,</u>
Line 32, replace "1)1" with -- 1,1 --.

<u>Column 11,</u>
Line 3, replace "arid" with -- and --.

<u>Column 14,</u>
Line 61, replace "C.," with -- C, --.

<u>Column 17,</u>
Line 39, replace "R24" with -- R19 --.
Line 55, replace "R17" with -- R27 --.

Signed and Sealed this

Ninth Day of September, 2003

JAMES E. ROGAN
*Director of the United States Patent and Trademark Office*